(12) United States Patent
Hamel et al.

(10) Patent No.: US 10,105,452 B2
(45) Date of Patent: Oct. 23, 2018

(54) METHODS AND PHARMACEUTICAL COMPOSITIONS FOR EXPRESSING A POLYNUCLEOTIDE OF INTEREST IN THE RETINAL PIGMENT EPITHELIUM OF A SUBJECT

(71) Applicants: INSERM (Institut National de la Sante et de la Recherche Medicale), Paris (FR); Centre Hospitalier Universitaire de Montpellier, Montpellier (FR); Universite de Montpellier, Montpellier (FR)

(72) Inventors: Christian Hamel, Montpellier (FR); Vasiliki Kalatzis, Montpellier (FR); Marie Pequignot, Montpellier (FR); Nicolas Cereso, Montpellier (FR)

(73) Assignees: INSERM (INSTITUT NATIONAL DE LA SANTÉ ET DE LA RECHERCHE MÉDICALE), Paris (FR); CENTRE HOSPITALIER UNIVERSITAIRE DE MONTPELLIER, Montpellier (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/101,591

(22) PCT Filed: Dec. 5, 2014

(86) PCT No.: PCT/EP2014/076740
§ 371 (c)(1),
(2) Date: Jun. 3, 2016

(87) PCT Pub. No.: WO2015/082690
PCT Pub. Date: Jun. 11, 2015

(65) Prior Publication Data
US 2016/0310618 A1    Oct. 27, 2016

(30) Foreign Application Priority Data
Dec. 6, 2013  (EP) .................................. 13306676

(51) Int. Cl.
| | | |
|---|---|---|
| *A61K 48/00* | (2006.01) |
| *C12N 9/10* | (2006.01) |
| *A61K 9/00* | (2006.01) |
| *A61K 31/713* | (2006.01) |
| *A61K 38/17* | (2006.01) |
| *C12N 7/00* | (2006.01) |
| *C12N 15/113* | (2010.01) |

(52) U.S. Cl.
CPC ........ *A61K 48/0058* (2013.01); *A61K 9/0019* (2013.01); *A61K 31/713* (2013.01); *A61K 38/1709* (2013.01); *A61K 48/005* (2013.01); *A61K 48/0066* (2013.01); *C12N 7/00* (2013.01); *C12N 9/10* (2013.01); *C12N 15/113* (2013.01); *C12N 2310/14* (2013.01); *C12N 2320/32* (2013.01); *C12N 2750/14132* (2013.01); *C12N 2750/14141* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | | |
|---|---|---|---|---|
| 2009/0202505 A1* | 8/2009 | Bartus et al. | ...... | A61K 31/7088 |
| 2011/0301073 A1 | 12/2011 | Gregory et al. | | |
| 2012/0172419 A1* | 7/2012 | Neitz et al. | .......... | A61B 5/0496 |

FOREIGN PATENT DOCUMENTS

| | | |
|---|---|---|
| WO | 2012/114090 A1 | 8/2012 |
| WO | 2012114090 | 8/2012 |

OTHER PUBLICATIONS

Lebherz et al.; "Novel AAV serotypes for improved ocular gene transfer"; Journal of Gene Medicine, vol. 10, No. 4, Jan. 1, 2008, pp. 375-382.
Allocca et al.; "Serotype-dependent packaging of large genes in adeno-associated viral vectors results in effective gene delivery in mice"; Journal of Clinical Investigation, vol. 118, No. 6, May 1, 2008, pp. 1955-1964.
Vasireddy et al.; "AAV-Mediated Gene Therapy for Choroideremia: Preclinical Studies in Personalized Models"; PLOS One, vol. 8, No. 5, May 7, 2013, pp. e61396 1-13.
Tolmachova et al.; "Functional expression of Rab escort protein 1 following AAV2-mediated gene delivery in the retina of choroideremia mice and human cells ex vivo"; Journal of Molecular Medicine, vol. 91, No. 7, Jun. 12, 2013, pp. 825-837.
Tolmachova et al.; "Retinal Pigment Epithelium Defects Accelerate Photoreceptor Degeneration in Cell Type-Specific Knockout Mouse Models of Choroideremia"; Investigative Ophthalmology & Visual Science, vol. 51, No. 10, Oct. 1, 2010, pp. 4913-4920.

(Continued)

*Primary Examiner* — James S Ketter
(74) *Attorney, Agent, or Firm* — W&C IP

(57) ABSTRACT

The present invention relates to methods and pharmaceutical compositions for expressing a polynucleotide of interest in the retinal pigment epithelium of a subject. In particular, the present invention relates to a method for selectively expressing a polynucleotide of interest in the retinal pigment epithelium in an eye of a subject in need thereof comprising the step of transducing the retinal pigment epithelium with an amount of a rAAV2/5 vector containing the polynucleotide of interest.

Figure 1A:
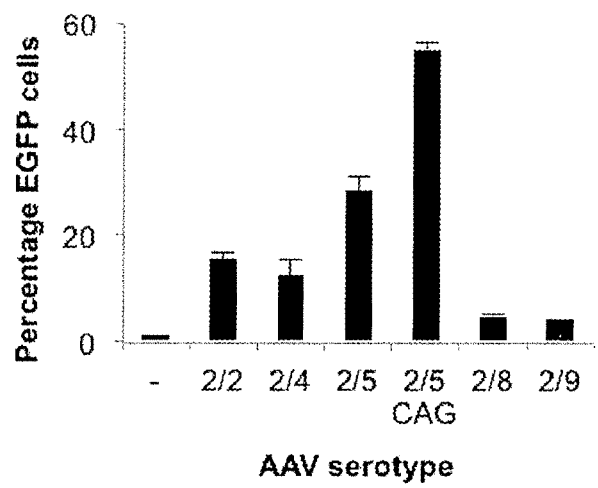

16 Claims, 6 Drawing Sheets
Specification includes a Sequence Listing.

(56) References Cited

OTHER PUBLICATIONS

International Search Report of related PCT Application WO/2015/082690.

Agbandje-McKenna et al., "AAV capsid structure and cell interactions". 2011. Methods Mol. Biol., vol. 807, p. 47-92.

Allocca et al., "Novel adeno-associated virus serotypes efficiently transduce murine photoreceptors". 2007. J. Virol., vol. 81, No. 20, p. 11372-11380.

Allocca et al., "Serotype-dependent packaging of large genes in adeno-associated viral vectors results in effective gene delivery in mice". 2008. J. Clinic. Invest., vol. 118, No. 5, p. 1955-1964.

Bainbridge et al., "Effect of gene therapy on visual function in Leber's congenital amaurosis". 2008. N. Engl. J. Med., vol. 358, No. 21, p. 2231-9.

Bennett et al., "AAV2 gene therapy readministration in three adults with congenital blindness". 2012. Sci. Transl. Med., vol. 4, No. 120, p. 120ra15.

Berger et al., "The molecular basis of human retinal and vitreoretinal diseases". 2010. Prog. Retin. Eye Res., 2010, vol. 29, No. 5, p. 335-375.

Bocquet et al., "Relative frequencies of inherited retinal dystrophies and optic neuropathies in Southern France: assessment of 21-year data management". 2013. Ophthalmic epidemiol., vol. 20, No. 1, p. 13-25.

Chekroud et al., "Simple and efficient: validation of a cotton wick electrode for animal electroretinography". 2011. Ophthalmic res., vol. 45, No. 4, p. 174-179.

Colella et al., "Ocular gene therapy: current progress and future prospects". 2009. Trends Mol. Med., vol. 15, No. 1, p. 23-31.

Egawa et al., "Drug screening for ALS using patient-specific induced pluripotent stem cells". 2012. Sci. Transl. Med., vol. 4, No. 145, p. 145ra104.

Grimm, "The art and design of genetic screens: mammalian culture cells". 2004. Nat Rev. Genet., vol. 5, p. 179-189.

Hauswirth et al., "Treatment of leber congenital amaurosis due to RPE65 mutations by ocular subretinal injection of adeno-associated virus gene vector: short-term results of a phase I trial". 2008. Hum. Gene Ther., vol. 19, No. 10, p. 979-990.

Jacobson et al., "Gene therapy for leber congenital amaurosis caused by RPE65 mutations: safety and efficacy in 15 children and adults followed up to 3 years". 2012. Arch. Ophthalmol., vol. 130, No. 1, p. 9-24.

Krock et al., "Noncell-autonomous photoreceptor degeneration in a zebrafish model of choroideremia". 2007. Proc. Natl. Acad. Sci. USA, vol. 104, No. 11, p. 4600-4605.

Lebherz et al., "Novel AAV serotypes for improved ocular gene transfer". 2008. J. Gene Med., vol. 10, No. 4, p. 375-82.

Liao et al., "Molecular signature of primary retinal pigment epithelium and stem-cell-derived RPE cells". 2010. Hum. Mol. Genet., vol. 19, No. 21, p. 4229-4238.

Maguire et al., "Age-dependent effects of RPE65 gene therapy for Leber's congenital amaurosis: a phase 1 dose-escalation trial". 2009. Lancet, vol. 374, No. 9701, p. 1597-1605.

Maguire et al., "Safety and efficacy of gene transfer for Leber's congenital amaurosis". 2008. N. Engl. J. Med., vol. 358, p. 2240-2248.

Marlhens et al., "Mutations in RPE65 cause Leber's congenital amaurosis". 1997. Nat. Genet., vol. 17, No. 2, p. 139-141.

Mussolino et al., "AAV-mediated photoreceptor transduction of the pig cone-enriched retina". 2011. Gene Ther., vol. 18, No. 7, p. 637-645.

Nicoud et al., "Development of photoreceptor-specific promoters and their utility to investigate EIAV lentiviral vector mediated gene transfer to photoreceptors". 2007. J. Gene Med., vol. 9, No. 12, 1015-23.

Park et al., "Reprogramming of human somatic cells to pluripotency with defined factors". 2008. Nature, vol. 451, No. 7175, p. 141-146.

Ramirez et al., "Side scatter intensity is highly heterogeneous in undifferentiated pluripotent stem cells and predicts clonogenic self-renewal". 2013. Stem Cells Dev., vol. 22, No. 12, p. 1851-1860.

Seabra et al., "Deficient geranylgeranylation of Ram/Rab27 in choroideremia". 1995. J. Biol. Chem., vol. 270, No. 41, p. 24420-24427.

Seabra et al., "Purification of component A of Rab geranylgeranyl transferase: possible identity with the choroideremia gene product". 1992. Cell, vol. 70, p. 1049-1057.

Siegel & Castellan, "Nonparametric statistics for the behavioral sciences". New York: McGraw-Hill. 1988.

Singh et al., "iPS cell modeling of Best disease: insights into the pathophysiology of an inherited macular degeneration". 2013. Hum. Mol. Genet., vol. 22, No. 3, p. 593-607.

Sparrow et al., "The retinal pigment epithelium in health and disease". 2010. Curr. Mol. Med., vol. 10, No. 9, p. 802-823.

Takahashi et al., "Induction of pluripotent stem cells from adult human fibroblasts by defined factors". 2007. Cell, vol. 131, No. 1, p. 861-872.

Tolmachova et al., "Functional expression of Rab escort protein 1 following AAV2-mediated gene delivery in the retina of choroideremia mice and human cells ex vivo". 2013. J. Mol. Med., vol. 91, No. 7, p. 825-837.

Tolmachova et al., "CHM/REP1 cDNA delivery by lentiviral vectors provides functional expression of the transgene in the retinal pigment epithelium of choroideremia mice". 2012. J. Gene Med., vol. 14, No. 3, p. 158-168.

Tolmachova et al., "Retinal pigment epithelium defects accelerate photoreceptor degeneration in cell type-specific knockout mouse models of choroideremia". 2010. Invest. Ophthalmol. Vis. Sci., vol. 51, No. 10, p. 4913-4920.

Tucker et al., "Transplantation of adult mouse iPS cell-derived photoreceptor precursors restores retinal structure and function in degenerative mice". 2011. PLoS One, vol. 6, p. el 8992.

Vandenberghe & Auricchio, "Novel adeno-associated viral vectors for retinal gene therapy". 2012. Gene Ther., vol. 19, No. 2, p. 162-168.

Vandenberghe et al., "Dosage thresholds for AAV2 and AAV8 photoreceptor gene therapy in monkey". 2011. Sci. Transl. Med., vol. 3, No. 88, p. 88ra54.

Vasireddy et al., "AAV-mediated gene therapy for choroideremia: preclinical studies in personalized models". 2013. PLoS One, vol. 8, No. 5, p. e61396.

Weber et al., "Recombinant adeno-associated virus serotype 4 mediates unique and exclusive long-term transduction of retinal pigmented epithelium in rat, dog, and nonhuman primate after subretinal delivery". 2003. Mol. Ther., vol. 7, p. 774-781.

Wu et al., "Synthesis of a fluorescent analogue of geranylgeranyl pyrophosphate and its use in a high-throughput fluorometric assay for Rab geranylgeranyltransferase". 2007. Nat. Protoc., vol. 2, No. 11, p. 2704-2711.

Young et al. "A short, highly active photoreceptor-specific enhancer/promoter region upstream of the human rhodopsin kinase gene". 2003. Invest. Ophthalmol. Vis. Sci., vol. 44, No. 9, p. 4076-85.

Yu & Thomson, "Pluripotent stem cell lines". 2008. Genes Dev., vol. 22, No. 15, p. 1987-1997.

Yu et al., "Induced pluripotent stem cell lines derived from human somatic cells". 2007. Science, vol. 318, No. 5858, p. 1917-1920.

Nguyen et al., "Analysis of protein prenylation in vitro and in vivo using functionalized phosphoisoprenoids". Curr. Protoc. Protein Sci., Chapt. 14, Unit 14.3 (Nov. 1, 2010).

* cited by examiner

```
SEQUENCE LISTING

<160> NUMBER OF SEQ ID NOS: 7

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ttcatctcct ttttgtgggg                                            20

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
ctggaaacat cctgtgttca tc                                         22

<210> SEQ ID NO 3
```

```
<211> LENGTH: 7
<212> TYPE: DNA
<213> ORGANISM: Homo sapiens

<400> SEQUENCE: 3 tagttct                                                                7

<210> SEQ ID NO 4
<211> LENGTH: 4
<212> TYPE: DNA
<213> ORGANISM: Homo sapiens

<400> SEQUENCE: 4 gatt                                                                   4

<210> SEQ ID NO 5
<211> LENGTH: 15
<212> TYPE: DNA
<213> ORGANISM: Homo sapiens

<400> SEQUENCE: 5
gtcatgcatt caatt                                                      15

<210> SEQ ID NO 6
<211> LENGTH: 653
<212> TYPE: PRT
<213> ORGANISM: Homo sapiens

<400> SEQUENCE: 6
```

Met Ala Asp Thr Leu Pro Ser Glu Phe Asp Val Ile Val Ile Gly Thr
1               5                  10                  15

Gly Leu Pro Glu Ser Ile Ile Ala Ala Cys Ser Arg Ser Gly Arg
            20                  25                  30

Arg Val Leu His Val Asp Ser Arg Ser Tyr Tyr Gly Gly Asn Trp Ala
        35                  40                  45

Ser Phe Ser Phe Ser Gly Leu Leu Ser Trp Leu Lys Glu Tyr Gln Glu
    50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
    130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
        195                 200                 205

Gln Pro Lys Lys Asn Arg Ile Thr Tyr Ser Gln Ile Ile Lys Glu Gly
    210                 215                 220

Arg Arg Phe Asn Ile Asp Leu Val Ser Lys Leu Leu Tyr Ser Arg Gly

```
                225                 230                 235                 240
        Leu Leu Ile Asp Leu Leu Ile Lys Ser Asn Val Ser Arg Tyr Ala Glu
                        245                 250                 255

Phe Lys Asn Ile Thr Arg Ile Leu Ala Phe Arg Glu Gly Arg Val Glu
                        260                 265                 270

Gln Val Pro Cys Ser Arg Ala Asp Val Phe Asn Ser Lys Gln Leu Thr
                        275                 280                 285

Met Val Glu Lys Arg Met Leu Met Lys Phe Leu Thr Phe Cys Met Glu
                        290                 295                 300

Tyr Glu Lys Tyr Pro Asp Glu Tyr Lys Gly Tyr Glu Glu Ile Thr Phe
        305                 310                 315                 320

Tyr Glu Tyr Leu Lys Thr Gln Lys Leu Thr Pro Asn Leu Gln Tyr Ile
                        325                 330                 335

Val Met His Ser Ile Ala Met Thr Ser Glu Thr Ala Ser Ser Thr Ile
                        340                 345                 350

Asp Gly Leu Lys Ala Thr Lys Asn Phe Leu His Cys Leu Gly Arg Tyr
                        355                 360                 365

Gly Asn Thr Pro Phe Leu Phe Pro Leu Tyr Gly Gln Gly Glu Leu Pro
                        370                 375                 380

Gln Cys Phe Cys Arg Met Cys Ala Val Phe Gly Gly Ile Tyr Cys Leu
        385                 390                 395                 400

Arg His Ser Val Gln Cys Leu Val Val Asp Lys Glu Ser Arg Lys Cys
                        405                 410                 415

Lys Ala Ile Ile Asp Gln Phe Gly Gln Arg Ile Ile Ser Glu His Phe
                        420                 425                 430

Leu Val Glu Asp Ser Tyr Phe Pro Glu Asn Met Cys Ser Arg Val Gln
                        435                 440                 445

Tyr Arg Gln Ile Ser Arg Ala Val Leu Ile Thr Asp Arg Ser Val Leu
                        450                 455                 460

Lys Thr Asp Ser Asp Gln Gln Ile Ser Ile Leu Thr Val Pro Ala Glu
        465                 470                 475                 480

Glu Pro Gly Thr Phe Ala Val Arg Val Ile Glu Leu Cys Ser Ser Thr
                        485                 490                 495

Met Thr Cys Met Lys Gly Thr Tyr Leu Val His Leu Thr Cys Thr Ser
                        500                 505                 510

Ser Lys Thr Ala Arg Glu Asp Leu Glu Ser Val Val Gln Lys Leu Phe
                        515                 520                 525

Val Pro Tyr Thr Glu Met Glu Ile Glu Asn Glu Gln Val Glu Lys Pro
                        530                 535                 540

Arg Ile Leu Trp Ala Leu Tyr Phe Asn Met Arg Asp Ser Ser Asp Ile
        545                 550                 555                 560

Ser Arg Ser Cys Tyr Asn Asp Leu Pro Ser Asn Val Tyr Val Cys Ser
                        565                 570                 575

Gly Pro Asp Cys Gly Leu Gly Asn Asp Asn Ala Val Lys Gln Ala Glu
                        580                 585                 590

Thr Leu Phe Gln Glu Ile Cys Pro Asn Glu Asp Phe Cys Pro Pro Pro
                        595                 600                 605

Pro Asn Pro Glu Asp Ile Ile Leu Asp Gly Asp Ser Leu Gln Pro Glu
                        610                 615                 620

Ala Ser Glu Ser Ser Ala Ile Pro Glu Ala Asn Ser Glu Thr Phe Lys
        625                 630                 635                 640

Glu Ser Thr Asn Leu Gly Asn Leu Glu Glu Ser Ser Glu
                        645                 650
```

<210> SEQ ID NO 7
<211> LENGTH: 5442
<212> TYPE: DNA
<213> ORGANISM: Homo sapiens

<400> SEQUENCE: 7

| | | | | | |
|---|---|---|---|---|---|
| taatagtcac | atgacacgtt | tcccgtcaag | atggcggata | ctctcccttc | ggagtttgat | 60 |
| gtgatcgtaa | tagggacggg | tttgcctgaa | tccatcattg | cagctgcatg | ttcaagaagt | 120 |
| ggccggagag | ttctgcatgt | tgattcaaga | agctactatg | gaggaaactg | gccagtttt | 180 |
| agcttttcag | gactattgtc | ctggctaaag | gaataccagg | aaaacagtga | cattgtaagt | 240 |
| gacagtccag | tgtggcaaga | ccagatcctt | gaaaatgaag | aagccattgc | tcttagcagg | 300 |
| aaggacaaaa | ctattcaaca | tgtggaagta | ttttgttatg | ccagtcagga | tttgcatgaa | 360 |
| gatgtcgaag | aagctggtgc | actgcagaaa | atcatgctc | ttgtgacatc | tgcaaactcc | 420 |
| acagaagctg | cagattctgc | cttcctgcct | acggaggatg | agtcattaag | cactatgagc | 480 |
| tgtgaaatgc | tcacagaaca | aactccaagc | agcgatccag | agaatgcgct | agaagtaaat | 540 |
| ggtgctgaag | tgacagggga | aaaagaaaac | cattgtgatg | ataaaacttg | tgtgccatca | 600 |
| acttcagcag | aagacatgag | tgaaaatgtg | cctatagcag | aagataccac | agagcaacca | 660 |
| aagaaaaaca | gaattactta | ctcacaaatt | attaaagaag | gcaggagatt | taatattgat | 720 |
| ttagtatcaa | agctgctgta | ttctcgagga | ttactaattg | atcttctaat | caaatctaat | 780 |
| gttagtcgat | atgcagagtt | taaaaatatt | accaggattc | ttgcatttcg | agaaggacga | 840 |
| gtggaacagg | ttccgtgttc | cagagcagat | gtctttaata | gcaaacaact | tactatggta | 900 |
| gaaaagcgaa | tgctaatgaa | atttcttaca | ttttgtatgg | aatatgagaa | atatcctgat | 960 |
| gaatataaag | gatatgaaga | gatcacattt | tatgaatatt | taaagactca | aaaattaacc | 1020 |
| cccaacctcc | aatatattgt | catgcattca | attgcaatga | catcagagac | agccagcagc | 1080 |
| accatagatg | gtctcaaagc | taccaaaaac | tttcttcact | gtcttgggcg | gtatggcaac | 1140 |
| actccatttt | tgtttccttt | atatggccaa | ggagaactcc | cccagtgttt | ctgcaggatg | 1200 |
| tgtgctgtgt | ttggtggaat | ttattgtctt | cgccattcag | tacagtgcct | tgtagtggac | 1260 |
| aaagaatcca | gaaaatgtaa | agcaattata | gatcagtttg | gtcagagaat | aatctctgag | 1320 |
| catttcctcg | tggaggacag | ttactttcct | gagaacatgt | gctcacgtgt | gcaatacagg | 1380 |
| cagatctcca | gggcagtgct | gattacagat | agatctgtcc | taaaaacaga | ttcagatcaa | 1440 |
| cagatttcca | ttttgacagt | gccagcgagg | gaaccaggaa | cttttgctgt | tcgggtcatt | 1500 |
| gagttatgtt | cttcaacgat | gacatgcatg | aaaggcacct | atttggttca | tttgacttgc | 1560 |
| acatcttcta | aaacgcaag | agaagattta | gaatcagttg | tgcagaaatt | gtttgttcca | 1620 |
| tatactgaaa | tggagataga | aaatgaacaa | gtagaaaagc | caagaattct | gtgggctctt | 1680 |
| tacttcaata | tgagagattc | gtcagacatc | agcaggagct | gttataatga | tttaccatcc | 1740 |
| aacgtttatg | tctgctctgg | cccagattgt | ggtttaggaa | atgataatgc | agtcaaacag | 1800 |
| gctgaaacac | ttttccagga | aatctgcccc | aatgaagatt | tctgtccccc | tccaccaaat | 1860 |
| cctgaagaca | ttatccttga | tggagacagt | ttacagccaa | ggcttcaga | atccagtgcc | 1920 |
| ataccagagg | ctaactcgga | gactttcaag | gaaagcacaa | accttggaaa | cctagaggag | 1980 |
| tcctctgaat | aatggatata | caccaaactg | gatacccaac | tttggaaatt | ctgactggtc | 2040 |
| tcagagtcta | cttgatagaa | ggactgtttg | agaaatgtta | gaaagcagca | gcaattataa | 2100 |

```
ggcaaaatag gtaatagaaa tccaaaaggg gatttteett atagaggaca ttccaagaac    2160
acacaacact tataaagcac attgacttgc tcattttaaa taccaaactt gtgtgactag    2220
cagatgaaaa ttataaatca attgattctc aggaatgtaa ctgtggatat gaaagtgatc    2280
ctatgcattg ttaataattc catggtctta ggacaatttt gcttaccact ttggatcttt    2340
gtttgaaagc cacattttca gaaccagctc atgtattttc tttggttatt tgaattttat    2400 tttcttatg gacaagagca tcataacata atgataaaaa catatagaaa aactaaagta     2460
tcatgatcta gatagaagcc tgtatttgga atacaggttt gttttgcttt ctatgttgag    2520
aagcattgaa aatgctaata taaggtgtt tagacatttt tacgaataag tcagtagtgt     2580
tttttagtat cagtagtgat atttgtttgt aaattattta catattggga aaggtcaata    2640
atgaagaaat gaagaatgg aaggaaaggt gtggataggc tcattggtat ttgaatattc     2700
tgtctgtcaa gtaactagag tattaggcta attgtctaca gacctaattt aatcctggct    2760
gtcctactga tgatatttgg taaattgttt aacttctgag cctacgtttc tccatatata    2820
aagtggaaat agtattacta tgcctactat atgagaatgg ttatgaagac aatgcaatgc    2880
catgtttaga atcggtttgc cagaagaaaa ttgttttaga attttcccat tgacttgatg    2940
aatctcaaaa gtctcacgca ggaaataatt gcttgctgtc agtcaacttc caaacaaaat    3000
agatcacagt gttttttattg cattaagctt tttaaatgaa aatttctttt ttaaagtagt   3060
attttatagt cttacagacc agtaaaaata gtaacaagta gaattgtggt tttgaaatat    3120
tactaaggaa aacactctat aaattgtttt attccttttc tggtaggtaa acctgcaacc    3180
accaaggact ccaaattgtg tatgacagtt ggtaagccct aatatacact acataaaaac    3240
gttagggctg cctgtaatcc cagcactttg ggaagctgag gtgggtagat cacttgaggt    3300
caggagttcg agaccagcct ggccaacatg gcgaaaccct gtctctacta aaaatacaaa    3360
attttagctg ggtgttatgg tgggcacctg taatcccagc tactttgaag atgaggtagc    3420
agactcactt gaaccaggga ggcggaggtt gcagtgagcc aagattttgc cactgcactc    3480
cagcctgggt gacagagcaa gactctgtct cacaaaaaaa aaaaaggggg gctgtacata    3540
ggcagcaaac taagctgcag tgatgttgcc tatatttaaa ttttctcaaa tggccaagct    3600
ctgatggtct actttatttg agcaatagtt gagacttata attgcctata aataaacaaa    3660
caaatgaact atttgttttt ttttctcaca acatctggcc tatattgtct gtcaggaagc    3720
catggctcca atgtaaagta catagttctt acatacttca actgcagctg gtccctgacc    3780
tcaccaggtt tcagagatgt tcttaaagga agccagctgt ggcaggtcac agattcatgg    3840
gaaatggaaa gaaccaagga atatagctct tgcctcacct ttctacccac tgcagatata    3900
gttcaagcca gagtaatgga agaacttaac ttactagcct ctcaggctgc tcctatccct    3960
acctcccagt gtacagcccc tccccatctc tttagtcccc tttccctcac ttccccttt     4020 ataatgtcac acaaatcagg gacagtagga tcacattata acctactttg tcatagggat    4080 tcgattttc ttatatcaaa tcatgtttcc tgaaacccag ctggggcata tgcactcaat     4140
gtctaataca tacttattaa tgtaccggat attggccttg cccctggata tcagcaatat    4200
attataaaag gttccagtag atgagacgat tgagtctgaa tacaattgca gtaaattgtg    4260
ccaataaaga tattgtactg ttacggtctt agagttaaag ccgcttgaat gcagcatgca    4320
cattcatgta aacagacaat cagggtaggc ctagaataac cacaaaaatt ctattggcct    4380
tactgcagcc acctatatgt agaacaatgg aaggagatagt ttgtggtcca ttattgtacc   4440
ctgtttcatc cattagcatc agaatctctc tttcaggtca tttattaaat atgattgaaa    4500
```

```
tgtttaaaag ttcctgaaca tgattcatga tgattaaaat atcatacaac tgataaaaga    4560
ctttaagaac tttatatatt tcctgttgcc tcaaaatgta acagaaatta ttcttagagc    4620
tttgatttta gctatcctaa ttactgcaaa taaatatttg ttcttatagt tttaaatcaa    4680
aaagaaaagt cttgttataa aaccttaagc ttgaaatcat attaataaaa tatattgtac    4740
atagtggaaa attttcagta gctaatttaa aatttcagaa aatgctatta aagaattttg    4800
attcaagtat ttaaactgtt tagttatgca tgcttcttat taaccgaaaa tgataatacc    4860
atttagttta gtgatcagta tgagaagcaa tacctaatcc tatgttgcta ttgtattttt    4920
tcctagttgg tgtgcctgct cagaaaaaca tatactgtat gtgtatacat acctgtgtat    4980 atataaagg tcaatttata tattttcta taggaaaatg gagtaacaag ttccctatct    5040
cccatattta tttgtccata gtaaaatggc cacattgatg ataatttcta gaactagttt    5100
ctgagattgt cagcccttg tctaaaataa tggcagtatt aatgattgac ttctgtcact    5160
gccatagtta cctggattgt cagccttggt agcctttgtc taaagtccta aagagttcca    5220
aaaaaaatgt gttgaaattt aattgctaaa tagtggttgg tgattcttta cagtaggaat    5280
tgtaataatt ttcttgcaaa taagttattt actgctattg atattgaata atttgtcttt    5340
tattcagata tatttcaaaa agcatgaata tatgattatt cataaattgt atactttacc    5400
agtaagtttt cagaggaaat aaagactttt aaatcctttt ca                      5442
```

METHODS AND PHARMACEUTICAL COMPOSITIONS FOR EXPRESSING A POLYNUCLEOTIDE OF INTEREST IN THE RETINAL PIGMENT EPITHELIUM OF A SUBJECT

FIELD OF THE INVENTION

The present invention relates to methods and pharmaceutical compositions for expressing a polynucleotide of interest in the retinal pigment epithelium of a subject.

BACKGROUND OF THE INVENTION

Inherited retinal dystrophies (IRDs) are a large group of diseases that are genetically and clinically heterogeneous. They are characterized by progressive vision loss, although the age at which legal blindness is reached is variable. Although individually rare, collectively IRDs affect approximately 1 in 2000 individuals worldwide (Berger et al, 2010). The most prevalent form of IRD is the group of pigmentary retinopathies, which are characterised by degeneration of the photoreceptor cells of the retina and the presence of pigment deposits visible on the fundus. A good example is choroideremia (CMH). CHM is an X-linked pigmentary retinopathy that represents 2% of IRDs (Bocquet et al, 2013). It is characterized by night blindness in childhood followed by progressive loss of the visual field resulting in blindness by 40 to 50 years of age. CHM has a characteristic phenotype, comprising pigment deposits and an atrophy of the choriocapillaris of the choroid, situated just behind the retina. There is a single causative gene, CHM, which encodes REP1, Rab escort protein-1 (Seabra et al, 1992) a ubiquitous chaperon protein allowing the correct prenylation of Rab GTPases and subsequent delivery to their membrane targets.

The retina in general is highly amenable to gene therapy because i) it is accessible via non-invasive routes, ii) it is small and enclosed allowing the use of low vector doses, and iii) the presence of a blood-retina barrier, composed of the tight junctions of the retinal pigment epithelium (RPE) and the non-fenestrated capillaries of the retinal circulation, prevents leakage into the circulation and renders it immuno-privileged (Colella et al, 2009). These positive attributes led to the first clinical trials for retinal gene therapy in 2008 (Bainbridge et al, 2008; Maguire et al, 2008) that were rapidly followed by others (Bennett et al, 2012; Hauswirth et al, 2008; Jacobson et al, 2012; Maguire et al, 2009). The target IRD, Leber congenital amaurosis (LCA), arises due to mutations in the RPE-specific gene, RPE65 (Marlhens et al, 1997), which encodes a key enzyme of the visual cycle. RPE65 was successfully vehicled into the RPE using a recombinant adeno-associated virus serotype 2 vector (AAV2/2). The positive results provided the proof-in-principle that gene transfer can ameliorate sight in visually impaired subjects and prompt the researchers to the identification of the most efficient vectors, especially for expression a polynucleotide of interest in RPE.

SUMMARY OF THE INVENTION

The present invention relates to methods and pharmaceutical compositions for expressing a polynucleotide of interest in the retinal pigment epithelium of a subject. In particular the present invention is defined by the claims.

DETAILED DESCRIPTION OF THE INVENTION

The inventors reprogrammed REP1-deficient fibroblasts from a CHM$^{-/y}$ patient into induced pluripotent stem cells (iPSc), which they differentiated into retinal pigment epithelium (RPE). They demonstrated that this iPSc-derived RPE is a polarised monolayer with a classical morphology, expresses characteristic markers, is functional for fluid transport and phagocytosis, and mimics the biochemical phenotype of patients. Then the inventors assayed a panel of AAV vector serotypes and showed for the first time that AAV2/5 was the most efficient (>60% transduction) on human RPE cells and that CHM gene transfer can normalise the biochemical phenotype. The high and unmatched in vitro transduction efficiency is likely aided by phagocytosis and mimics the scenario an AAV vector encounters in vivo in the subretinal space. The inventors thus demonstrate the superiority of AAV2/5 in human control and CHM RPE.

Accordingly a first aspect of the invention relates to a method for selectively expressing a polynucleotide of interest in the retinal pigment epithelium in an eye of a subject in need thereof comprising the step of transducing the retinal pigment epithelium with an amount of a rAAV2/5 vector containing the polynucleotide of interest.

As used herein, the term "subject" or "subject in need thereof", is intended for a human. Typically the subject is affected or likely to be affected with a retinal disease affecting the retinal pigment epithelium. Accordingly a wide variety of retinal diseases may thus be treated given the teachings provided herein and typically include inherited or non-inherited retinal degenerations, retinal dystrophies, retinitis pigmentosa, macular degenerations, Leber's congenital amaurosis (LCA), cone-rod dystrophies, neovascular diseases of the eye, choroidal degenerations, choroidal sclerosis, diabetic retinopathies, proliferative vitreoretinopathies, choroideremia, glaucoma and metabolic disorders such as Sly syndrome (MPS VII, due to a defect in the beta-glucoronidase gene) and gyrate atrophy (due to a defect in the ornithine-delta-aminotransferase gene, OAT), retinal detachment or injury and retinopathies (whether inherited, induced by surgery, trauma, a toxic compound or agent, or light induced).

Accordingly, another object of this invention is to provide a method for treating a retinal disease in a subject in need thereof, by delivering into the eye of the subject a rAAV2/5 vector comprising a polynucleotide of interest which when expressed in RPE cells, has a beneficial effect on the retinal disease.

Accordingly, another object of this invention is to provide a method for treating a retinal disease in a subject in need thereof, by delivering into the eye of the subject a rAAV2/5 vector comprising a polynucleotide of interest which when expressed in RPE cells, has a beneficial effect on the retinal disease.

As used herein the expression "polynucleotide of interest" herein designates any nucleotide sequence coding for any polypeptide, structural protein, enzyme etc., the expression of which is wanted in a target cell, for any kind of reason. It can also designate a non-coding sequence, for example an antisense sequence or the sequence of an interfering RNA aimed at decreasing the expression of a gene. One skilled in the art knows, by its knowledge of the scientific literature in his field, which are the polynucleotides that may be more appropriate to treat a specific retinal disease.

Gene therapy of the eye with rAAV2/5 vectors of the present invention can be performed either by introducing in RPE cells a functional copy of a polynucleotide of interest (e.g. a gene) that is deficient therein (gene replacement therapy), or by delivering to RPE cells a polynucleotide of interest which will have a beneficial effect on the eye disease to be treated (symptomatic therapy).

In a particular the polynucleotide product is a polypeptide that will enhance the function of retinal pigment epithelial cells. Examples of polynucleotides of interest that can be used for gene replacement therapy are genes that are specifically or preferentially expressed in RPE cells, such as RGR (Retinitis pigmentosa, RP, chromosome (chr.) 10), RDH5 (fundus albipunctatus, chr. 12), RPE65 (Leber's congenital amaurosis, LCA, chr. 1), RLBP1 (RP, chr. 15), MERTK (RP, chr. 2), LRAT (RP, chr. 4), REP1 (choroideremia, Xp21), RBP4 (RPE degeneration, chr. 10) or genes that are also expressed in other cell-types, such as MYO7A (Usher syndrome type 1, chr. 11), ELOVL4 (macular degeneration, chr. 6), EFEMP1 (Malattia Leventinese disease, chr. 15), BEST1 (Best Disease, chr. 11), TIMP3 (Sorsby's fundus dystrophy, chr. 22), AIPL1 (LCA, chr. 7), and CRB1 (RP, chr. 1).

In some embodiments, the polynucleotide is a polynucleotide encoding for REP1, Rab escort protein-1 (i.e. a CHM gene).

In a particular embodiment, the polynucleotide of interest may encode for a neurotrophic factor. As used herein, the "neurotrophic factor" is a generic term of proteins having a physiological action such as survival and maintenance of nerve cells, promotion of neuronal differentiation. Examples of neurotrophic factors include but are not limited to bFGF, aFGF, BDNF, CNTF, IL-1beta, NT-3, IGF-II, GDNF, NGF and RdCVF.

In certain circumstances, the polynucleotide product of interest is a site-specific endonuclease that provides for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease (such as TALEnucleases, meganucleases or Zinc finger nucleases) can be targeted to the defective allele and knock out the defective allele. In addition to knocking out a defective allele, a site-specific nuclease can also be used to stimulate homologous recombination with a donor DNA that encodes a functional copy of the protein encoded by the defective allele. Thus, for example, the method of the invention can be used to deliver both a site-specific endonuclease that knocks out a defective allele, and can be used to deliver a functional copy of the defective allele, resulting in repair of the defective allele, thereby providing for production of a functional retinal protein. In some embodiments, the vector comprises a polynucleotide that encodes a site-specific endonuclease; and a polynucleotide that encodes a functional copy of a defective allele, where the functional copy encodes a functional retinal protein. Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

In some embodiments, the polynucleotide product is an interfering RNA (RNAi).

As used herein the term "AAV" has its general meaning in the art and is an abbreviation for adeno-associated virus, and may be used to refer to the virus itself or derivatives thereof The term covers all serotypes and variants both naturally occurring and engineered forms. According to the invention the term "AAV" refers to AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), and AAV type 8 (AAV-8) and AAV type 9 (AAV9). The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_001401 (AAV-2), AF043303 (AAV2), and NC_006152 (AAV-5).

As used herein, a "rAAV vector" refers to an AAV vector comprising the polynucleotide of interest (i.e a heterologous polynucleotide) for the genetic transformation of a RPE cell. The rAAV vectors contain 5' and 3' adeno-associated virus inverted terminal repeats (ITRs), and the polynucleotide of interest operatively linked to sequences, which regulate its expression in a target cell.

The phrase "AAV hybrid vector", herein designates a vector particle comprising a native AAV capsid including an rAAV vector genome and AAV Rep proteins, wherein Cap, Rep and the ITRs of the vector genome come from at least 2 different AAV serotypes. The hybrid vector of the invention is a rAAV2/5 vector, comprising an AAV-5 capsid and a rAAV genome with AAV-2 ITRs. For example, it is possible to derive a cap gene from the cap gene of AAV-2 by replacing it with a sequence from the cap gene of AAV-5, in such a way that the expressed proteins are able to form a capsid an AAV-5 capsid.

The rAAV2/5 vectors of the invention are produced using methods known in the art. In short, the methods generally involve (a) the introduction of the rAAV vector into a host cell, (b) the introduction of an AAV helper construct into the host cell, wherein the helper construct comprises the viral functions missing from the rAAV vector and (c) introducing a helper virus into the host cell. All functions for rAAV virion replication and packaging need to be present, to achieve replication and packaging of the rAAV vector into rAAV virions. The introduction into the host cell can be carried out using standard virological techniques simultaneously or sequentially. Finally, the host cells are cultured to produce rAAV virions and are purified using standard techniques such as CsCl gradients. Residual helper virus activity can be inactivated using known methods, such as for example heat inactivation. The purified rAAV virion is then ready for use in the methods.

The vector may also comprise regulatory sequences allowing expression and, secretion of the encoded protein, such as e.g., a promoter, enhancer, polyadenylation signal, internal ribosome entry sites (IRES), sequences encoding protein transduction domains (PTD), and the like. In this regard, the vector comprises a promoter region, operably linked to the polynucleotide of interest, to cause or improve expression of the protein in infected cells. Such a promoter may be ubiquitous, tissue-specific, strong, weak, regulated, chimeric, inducible, etc., to allow efficient and suitable production of the protein in the infected tissue.

The promoter may be homologous to the encoded protein, or heterologous, including cellular, viral, fungal, plant or synthetic promoters. The preferred promoters for use in the present invention should be functional in RPE cells. Examples of such regulated promoters include, without limitation, Tet on/off element-containing promoters, rapamycin-inducible promoters and metallothionein promoters. Examples of ubiquitous promoters include viral promoters, particularly the CMV promoter, CAG promoter (chicken beta actin promoter with CMV enhancer), the RSV promoter, the SV40 promoter, etc. and cellular promoters such as the PGK (phosphoglycerate kinase) promoter. The promoters may also be neurospecific promoters such as the Synapsin or the NSE (Neuron Specific Enolase) promoters (or NRSE (Neuron restrictive silencer element) sequences placed upstream from the ubiquitous PGK promoter), or promoters specific for RPE cell types such as the RPE65, the BEST1, the Rhodopsin or the cone arrestin promoters. The vector may also comprise target sequences for miRNAs achieving suppression of transgene expression in nondesired cells. In a particular embodiment, the vector comprises a leader sequence allowing secretion of the encoded protein. Fusion of the polynucleotide of interest with a sequence encoding a secretion signal peptide (usually located at the N-terminal end of secreted polypeptides) will allow the production of the therapeutic protein in a form that can be secreted from the transduced cells. Examples of such signal peptides include the albumin, the β-glucuronidase, the alkaline protease or the fibronectin secretory signal peptides. In a most preferred embodiment, the promoter is specific or functional in cells of the retina, in particular in photoreceptor or ganglion cells of the retina or in the RPE, i.e., allows (preferential) expression of the transgene in said cells. For example, suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9: 1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225).

The doses of vectors may be adapted depending on the disease condition, the subject (for example, according to his weight, metabolism, etc.), the treatment schedule, etc. A preferred effective dose within the context of this invention is a dose allowing an optimal transduction of the RPE cells. Typically, from $10^8$ to $10^{10}$ viral genomes (vg) are administered per dose in mice. Typically, the doses of AAV vectors to be administered in humans may range from $10^{10}$ to $10^{12}$ vg.

Administering the vector of the invention vector to the subject may be done by direct retinal, subretinal or intravitreal injection. According to this method, the administration of the vector particle is preferably performed by subretinal delivery.

In some aspects, the present invention relates to a rAAV2/5 vector containing a polynucleotide encoding for REP1. In some embodiments the polynucleotide is under the control of a CAG promoter. Said vector is particularly suitable for treating choroideremia in a subject in need thereof.

An exemplary amino acid sequence for REP1 is SEQ ID NO:6 and an exemplary nucleic sequence for REP1 is SEQ ID NO:7.

SEQ ID NO: 6: NCBI Reference Sequence:
NP_001138886.1
MADTLPSEFD VIVIGTGLPE SIIAAACSRS GRRVLHVDSR

SYYGGNWASF SFSGLLSWLK EYQENSDIVS DSPVWQDQIL

ENEEAIALSR KDKTIQHVEV FCYASQDLHE DVEEAGALQK

-continued
NHALVTSANS TEAADSAFLP TEDESLSTMS CEMLTEQTPS

SDPENALEVN GAEVTGEKEN HCDDKTCVPS TSAEDMSENV

PIAEDTTEQP KKNRITYSQI IKEGRRFNID LVSKLLYSRG

LLIDLLIKSN VSRYAEFKNI TRILAFREGR VEQVPCSRAD

VFNSKQLTMV EKRMLMKFLT FCMEYEKYPD EYKGYEEITF

YEYLKTQKLT PNLQYIVMHS IAMTSETASS TIDGLKATKN

FLHCLGRYGN TPFLFPLYGQ GELPQCFCRM CAVFGGIYCL

RHSVQCLVVD KESRKCKAII DQFGQRIISE HFLVEDSYFP

ENMCSRVQYR QISRAVLITD RSVLKTDSDQ QISILTVPAE

EPGTFAVRVI ELCSSTMTCM KGTYLVHLTC TSSKTAREDL

ESVVQKLFVP YTEMEIENEQ VEKPRILWAL YFNMRDSSDI

SRSCYNDLPS NVYVCSGPDC GLGNDNAVKQ AETLFQEICP

NEDFCPPPPN PEDIILDGDS LQPEASESSA IPEANSETFK

ESTNLGNLEE SSE

SEQ ID NO: 7: NCBI Reference Sequence:
NM_000390.2
TAATAGTCAC ATGACACGTT TCCCGTCAAG ATGGCGGATA

CTCTCCCTTC GGAGTTTGAT GTGATCGTAA TAGGGACGGG

TTTGCCTGAA TCCATCATTG CAGCTGCATG TTCAAGAAGT

GGCCGGAGAG TTCTGCATGT TGATTCAAGA AGCTACTATG

GAGGAAACTG GGCCAGTTTT AGCTTTTCAG GACTATTGTC

CTGGCTAAAG GAATACCAGG AAAACAGTGA CATTGTAAGT

GACAGTCCAG TGTGGCAAGA CCAGATCCTT GAAAATGAAG

AAGCCATTGC TCTTAGCAGG AAGGACAAAA CTATTCAACA

TGTGGAAGTA TTTTGTTATG CCAGTCAGGA TTTGCATGAA

GATGTCGAAG AAGCTGGTGC ACTGCAGAAA AATCATGCTC

TTGTGACATC TGCAAACTCC ACAGAAGCTG CAGATTCTGC

CTTCCTGCCT ACGGAGGATG AGTCATTAAG CACTATGAGC

TGTGAAATGC TCACAGAACA AACTCCAAGC AGCGATCCAG

AGAATGCGCT AGAAGTAAAT GGTGCTGAAG TGACAGGGGA

AAAAGAAAAC CATTGTGATG ATAAAACTTG TGTGCCATCA

ACTTCAGCAG AAGACATGAG TGAAAATGTG CCTATAGCAG

AAGATACCAC AGAGCAACCA AAGAAAAACA GAATTACTTA

CTCACAAATT ATTAAAGAAG GCAGGAGATT TAATATTGAT

TTAGTATCAA AGCTGCTGTA TTCTCGAGGA TTACTAATTG

ATCTTCTAAT CAAATCTAAT GTTAGTCGAT ATGCAGAGTT

TAAAAATATT ACCAGGATTC TTGCATTTCG AGAAGGACGA

GTGGAACAGG TTCCGTGTTC CAGAGCAGAT GTCTTTAATA

GCAAACAACT TACTATGGTA GAAAAGCGAA TGCTAATGAA

ATTTCTTACA TTTTGTATGG AATATGAGAA ATATCCTGAT

GAATATAAAG GATATGAAGA GATCACATTT TATGAATATT

TAAAGACTCA AAAATTAACC CCCAACCTCC AATATATTGT

```
CATGCATTCA ATTGCAATGA CATCAGAGAC AGCCAGCAGC
ACCATAGATG GTCTCAAAGC TACCAAAAAC TTTCTTCACT
GTCTTGGGCG GTATGGCAAC ACTCCATTTT TGTTTCCTTT
ATATGGCCAA GGAGAACTCC CCCAGTGTTT CTGCAGGATG
TGTGCTGTGT TTGGTGGAAT TTATTGTCTT CGCCATTCAG
TACAGTGCCT TGTAGTGGAC AAAGAATCCA GAAAATGTAA
AGCAATTATA GATCAGTTTG GTCAGAGAAT AATCTCTGAG
CATTTCCTCG TGGAGGACAG TTACTTTCCT GAGAACATGT
GCTCACGTGT GCAATACAGG CAGATCTCCA GGGCAGTGCT
GATTACAGAT AGATCTGTCC TAAAAACAGA TTCAGATCAA
CAGATTTCCA TTTTGACAGT GCCAGCAGAG GAACCAGGAA
CTTTTGCTGT TCGGGTCATT GAGTTATGTT CTTCAACGAT
GACATGCATG AAAGGCACCT ATTTGGTTCA TTTGACTTGC
ACATCTTCTA AAACAGCAAG AGAAGATTTA GAATCAGTTG
TGCAGAAATT GTTTGTTCCA TATACTGAAA TGGAGATAGA
AAATGAACAA GTAGAAAAGC CAAGAATTCT GTGGGCTCTT
TACTTCAATA TGAGAGATTC GTCAGACATC AGCAGGAGCT
GTTATAATGA TTTACCATCC AACGTTTATG TCTGCTCTGG
CCCAGATTGT GGTTTAGGAA ATGATAATGC AGTCAAACAG
GCTGAAACAC TTTTCCAGGA AATCTGCCCC AATGAAGATT
TCTGTCCCCC TCCACCAAAT CCTGAAGACA TTATCCTTGA
TGGAGACAGT TTACAGCCAG AGGCTTCAGA ATCCAGTGCC
ATACCAGAGG CTAACTCGGA GACTTTCAAG GAAAGCACAA
ACCTTGGAAA CCTAGAGGAG TCCTCTGAAT AATGGATATA
CACCAAACTG GATACCCAAC TTTGGAAATT CTGACTGGTC
TCAGAGTCTA CTTGATAGAA GGACTGTTTG AGAAATGTTA
GAAAGCAGCA GCAATTATAA GGCAAATAG GTAATAGAAA
TCCAAAAGGG GATTTTCCTT ATAGAGGACA TTCCAAGAAC
ACACAACACT TATAAAGCAC ATTGACTTGC TCATTTTAAA
TACCAAACTT GTGTGACTAG CAGATGAAAA TTATAAATCA
ATTGATTCTC AGGAATGTAA CTGTGGATAT GAAAGTGATC
CTATGCATTG TTAATAATTC CATGGTCTTA GGACAATTTT
GCTTACCACT TTGGATCTTT GTTTGAAAGC CACATTTTCA
GAACCAGCTC ATGTATTTTC TTTGGTTATT TGAATTTTAT
TTTCTTTATG GACAAGAGCA TCATAACATA ATGATAAAAA
CATATAGAAA AACTAAAGTA TCATGATCTA GATAGAAGCC
TGTATTTGGA ATACAGGTTT GTTTTGCTTT CTATGTTGAG
AAGCATTGAA AATGCTAATA TAAAGGTGTT TAGACATTTT
TACGAATAAG TCAGTAGTGT TTTTTAGTAT CAGTAGTGAT
ATTTGTTTGT AAATTATTTA CATATTGGGA AAGGTCAATA

ATGAAGAAAT GAAAGAATGG AAGGAAAGGT GTGGATAGGC
TCATTGGTAT TTGAATATTC TGTCTGTCAA GTAACTAGAG
TATTAGGCTA ATTGTCTACA GACCTAATTT AATCCTGGCT
GTCCTACTGA TGATATTTGG TAAATTGTTT AACTTCTGAG
CCTACGTTTC TCCATATATA AAGTGGAAAT AGTATTACTA
TGCCTACTAT ATGAGAATGG TTATGAAGAC AATGCAATGC
CATGTTTAGA ATCGGTTTGC CAGAAGAAAA TTGTTTTAGA
ATTTTCCCAT TGACTTGATG AATCTCAAAA GTCTCACGCA
GGAAATAATT GCTTGCTGTC AGTCAACTTC CAAACAAAAT
AGATCACAGT GTTTTTATTG CATTAAGCTT TTTAAATGAA
AATTTCTTTT TTAAAGTAGT ATTTTATAGT CTTACAGACC
AGTAAAAATA GTAACAAGTA GAATTGTGGT TTTGAAATAT
TACTAAGGAA AACACTCTAT AAATTGTTTT ATTCCTTTTC
TGGTAGGTAA ACCTGCAACC ACCAAGGACT CCAAATTGTG
TATGACAGTT GGTAAGCCCT AATATACACT ACATAAAAAC
GTTAGGGCTG CCTGTAATCC CAGCACTTTG GGAAGCTGAG
GTGGGTAGAT CACTTGAGGT CAGGAGTTCG AGACCAGCCT
GGCCAACATG GCGAAACCCT GTCTCTACTA AAAATACAAA
ATTTTAGCTG GGTGTTATGT GGGCACCTG TAATCCCAGC
TACTTTGAAG ATGAGGTAGC AGACTCACTT GAACCAGGGA
GGCGGAGGTT GCAGTGAGCC AAGATTTTGC CACTGCACTC
CAGCCTGGGT GACAGAGCAA GACTCTGTCT CACAAAAAAA
AAAAAAGGGG GCTGTACATA GGCAGCAAAC TAAGCTGCAG
TGATGTTGCC TATATTTAAA TTTTCTCAAA TGGCCAAGCT
CTGATGGTCT ACTTTATTTG AGCAATAGTT GAGACTTATA
ATTGCCTATA AATAAACAAA CAAATGAACT ATTTGTTTTT
TTTTCTCACA ACATCTGGCC TATATTGTCT GTCAGGAAGC
CATGGCTCCA ATGTAAAGTA CATAGTTCTT ACATACTTCA
ACTGCAGCTG GTCCCTGACC TCACCAGGTT TCAGAGATGT
TCTTAAAGGA AGCCAGCTGT GGCAGGTCAC AGATTCATGG
GAAATGGAAA GAACCAAGGA ATATAGCTCT TGCCTCACCT
TTCTACCCAC TGCAGATATA GTTCAAGCCA GAGTAATGGA
AGAACTTAAC TTACTAGCCT CTCAGGCTGC TCCTATCCCT
ACCTCCCAGT GTACAGCCCC TCCCCATCTC TTTAGTCCCC
TTTCCCTCAC TTCCCCTTTT ATAATGTCAC ACAAATCAGG
GACAGTAGGA TCACATTATA ACCTACTTTG TCATAGGGAT
TCGATTTTTC TTATATCAAA TCATGTTTCC TGAAACCCAG
CTGGGGCATA TGCACTCAAT GTCTAATACA TACTTATTAA
TGTACCGGAT ATTGGCCTTG CCCCTGGATA TCAGCAATAT
ATTATAAAAG GTTCCAGTAG ATGAGACGAT TGAGTCTGAA
TACAATTGCA GTAAATTGTG CCAATAAAGA TATTGTACTG
```

-continued

```
TTACGGTCTT AGAGTTAAAG CCGCTTGAAT GCAGCATGCA

CATTCATGTA AACAGACAAT CAGGGTAGGC CTAGAATAAC

CACAAAAATT CTATTGGCCT TACTGCAGCC ACCTATATGT

AGAACAATGG AGGAGATAGT TTGTGGTCCA TTATTGTACC

CTGTTTCATC CATTAGCATC AGAATCTCTC TTTCAGGTCA

TTTATTAAAT ATGATTGAAA TGTTTAAAAG TTCCTGAACA

TGATTCATGA TGATTAAAAT ATCATACAAC TGATAAAAGA

CTTTAAGAAC TTTATATATT TCCTGTTGCC TCAAAATGTA

ACAGAAATTA TTCTTAGAGC TTTGATTTTA GCTATCCTAA

TTACTGCAAA TAAATATTTG TTCTTATAGT TTTAAATCAA

AAAGAAAGT CTTGTTATAA AACCTTAAGC TTGAAATCAT

ATTAATAAAA TATATTGTAC ATAGTGGAAA ATTTTCAGTA

GCTAATTTAA AATTTCAGAA AATGCTATTA AAGAATTTTG

ATTCAAGTAT TTAAACTGTT TAGTTATGCA TGCTTCTTAT

TAACCGAAAA TGATAATACC ATTTAGTTTA GTGATCAGTA

TGAGAAGCAA TACCTAATCC TATGTTGCTA TTGTATTTTT

TCCTAGTTGG TGTGCCTGCT CAGAAAAACA TATACTGTAT

GTGTATACAT ACCTGTGTAT ATATAAAAGG TCAATTTATA

TATTTTTCTA TAGGAAAATG GAGTAACAAG TTCCCTATCT

CCCATATTTA TTTGTCCATA GTAAAATGGC CACATTGATG

ATAATTTCTA GAACTAGTTT CTGAGATTGT CAGCCCTTTG

TCTAAAATAA TGGCAGTATT AATGATTGAC TTCTGTCACT

GCCATAGTTA CCTGGATTGT CAGCCTTGGT AGCCTTTGTC

TAAAGTCCTA AAGAGTTCCA AAAAAAATGT GTTGAAATTT

AATTGCTAAA TAGTGGTTGG TGATTCTTTA CAGTAGGAAT

TGTAATAATT TTCTTGCAAA TAAGTTATTT ACTGCTATTG

ATATTGAATA ATTTGTCTTT TATTCAGATA TATTTCAAAA

AGCATGAATA TATGATTATT CATAAATTGT ATACTTTACC

AGTAAGTTTT CAGAGGAAAT AAAGACTTTT AAATCCTTTT

CA
```

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient (i.e. the vector of the invention). The precise nature of the carrier or other material may be determined by the skilled person according to the route of administration, i.e. here direct retinal, subretinal or intravitreal injection. The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. For injection, the active ingredient will be in the form of an aqueous solution, which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. For delayed release, the vector may be included in a pharmaceutical composition, which is formulated for slow release, such as in microcapsules formed from biocompatible polymers or in liposomal carrier systems according to methods known in the art.

The invention will be further illustrated by the following figures and examples. However, these examples and figures should not be interpreted in any way as limiting the scope of the present invention.

FIGURES

FIG. 1: Transduction efficiency of AAV vectors in the iPSc-derived RPE. a) Comparison of the transduction efficiency of a panel of AAV vectors (2/2, 2/4, 2/5, 2/8, 2/9) expressing EGFP under control of the CMV promoter. This transduction efficiency was also compared to an AAV2/5 vector expressing EGFP under control of the CAG promoter. Transduction was performed with 25 000 vg/cell and the number of EGFP-positive cells was analysed by FACS. b) Comparison of the transduction efficiency achieved using a higher number of viral particles (100 000 vg/cell) of the AAV vectors 2/2, 2/5, 2/8, 2/9 expressing EGFP under control of the CMV promoter. The number of EGFP-positive cells was analysed by FACS. c) A time course of EGFP expression from the same panel of AAV vectors. d) Wild-type and CHM1 RPE is transduced at an equal efficiency by AA2/5-CAG-EGFP.

FIG. 2: REP1 expression from the vector AAV2/5-CAG-CHM in CHM1 fibroblasts. a) IF studies of REP1 expression in wild-type fibroblasts. b) Absence of REP1 expression in CHM1 fibroblasts. c) REP1 expression from AAV2/5-CAG-CHM 48 h post-transduction of CHM1 fibroblasts with 100 000 vg/cell. d) Western blot analysis of fibroblasts 48 h post-transduction with 100 000 vg/cell of AAV2/5-CAG-CHM showed that REP1 was expressed at a level of approximately 17% of wild-type (WT). e) Western blot analysis of RPE 4-wks post-transduction with 100 000 vg/cell of AAV2/5-CAG-CHM showed that REP1 was expressed at a level of approximately 53% of wild-type. Note the absence of REP1 expression in non-transduced (NT) CHM1 cells in both d) and e).

FIG. 3: Restoration of a normal cellular phenotype in CHM RPE following transduction with AAV2/5-CAG-CHM. A) In vitro prenylation followed by western blot analysis of incorporated biotinylated prenyl donor in wild-type, non-transduced CHM1 RPE and CHM1 RPE transduced with AAV2/5-CAG-CHM. B) Differential centrifugation and western blot analysis of cytosolic and membrane fractions in wild-type, non-transduced CHM1 RPE and CHM1 RPE transduced with AAV2/5-CAG-CHM or AAV2/5-CAG-EGFP. C) Quantification following normalisation to beta-actin loading levels indicated a reduction of the cytosolic Rab pool to wild-type levels following transduction of CHM1 RPE with AAV2/5-CAG-CHM. D) Quantification analysis indicated a restoration of the subcellular distribution profile of Rab27A to wild-type levels following transduction of CHM1 RPE with AAV2/5-CAG-CHM. In contrast, levels were unchanged following transduction with AAV2/5-CAG-EGFP.

FIG. 4: In vivo gene transfer in the mouse retina. a) Two-weeks post-administration of $4.68 \times 10^9$ vg of AAV5-CAG-CHM or -EGFP, transgene expression could be detected by q-PCR studies. b) Western blot analysis confirmed the specific expression of REP1 and EGFP after administration of AAV5-CAG-CHM or -EGFP, respectively. c) Funduscopy studies showed a healthy retina beyond the injection site following administration of AAV5-CAG-CHM and widespread transgene expression, stronger at the injection site, following injection of AAV5-CAG-EGFP. d) EGFP expression was detected along the whole retina on the side of optic nerve, which housed the injection site (scale bar); inset, the magnification showing EGFP expression in the RPE and the photoreceptors.

EXAMPLE

Material & Methods

Isolation and Amplification of Skin Fibroblasts

Skin biopsies were performed under sterile conditions on the inner side of the upper arm of a 16-year-old boy (referred to as CHM1) with a confirmed molecular diagnosis (deletion of exon 8 of CHM identified by RT-PCR; Klinkum der Universitat, Regensburg, Germany) of choroideremia at the Centre of Reference for Genetic Sensory Disorders (CHRU Montpellier) Skin biopsies were rinsed in PBS, cut into small pieces and cultured in a 35 mm culture dishes (2 pieces per dish) in AmnioMAX C100 basal media with L-glutamine (Invitrogen, Life Technologies, Saint Aubin, France) containing 10% decomplemented FCS (Lonza, Verviers, Belgium), 1% penicillin-streptomycin-amphotericin B (Lonza) and 2% AmnioMax-C100 supplement (Invitrogen, Life Technologies) at 37° C. under 5% CO2. The biopsies were removed to a fresh dish once the emerging fibroblasts reached 80% confluence. The biopsies were transferred 4 times in total and cells ranging from P1 to P5 from each separate culture were frozen in FCS containing 10% DMSO (Sigma Aldrich, Saint Quentin Fallavier, France).

Mutation Characterisation

Genomic DNA was isolated from primary fibroblasts using the DNeasy Blood & Tissue Kit (Qiagen, Les Ulis, France) according to the manufacturer's instructions. To define the borders of the exon 8 deletion in CHM carried by the CHM patient, 3 primers pairs distributed over 1.6 kb of genomic DNA 5' to exon 8, and 8 primer pairs distributed over 38 kb 3' to exon 8 were tested for PCR amplification of control and patient DNA using standard conditions. Once a reduced interval was established, an intron 7 F primer (5'-TTC-ATCTCC-TTT-TTG-TGG-GG-3') (SEQ ID NO:1) situated 78 by upstream of exon 8 and an intron 8 R primer (5'-CTG-GAA-ACA-TCC-TGT-GTT-CAT-C-3') (SEQ ID NO:2) situated 362-bp downstream of exon 8 were used to amplify a 666-bp genomic DNA fragment that was purified using an ExoSAP-IT PCR Clean-up Kit (GE Healthcare, Velizy Villacoublay, France) prior to sequencing using the BigDye Terminator Cycle Sequencing Ready Reaction kit V3.1 on an Applied Biosystems 3130xL Genetic Analyser (Applied Biosystems, Foster City, Calif., USA).

Mutation Detection

Three primer pairs were used for the PCR amplification of exons 7, 8 and 9 to test for the presence of the CHM deletion in genomic DNA from different cell types. The primer pairs for exon 7 amplified a 493-bp fragment, exon 8 amplified a 177-bp fragment, and exon 9 amplified a 975-bp fragment. RNA was isolated from different cell types using the QiaShredder and RNeasy mini kits (Qiagen) according to the manufacturer's instructions. The isolated RNA was treated with RNase-Free DNase (Qiagen) and reverse transcribed using the Superscript III Reverse Transcriptase kit (Life Technologies). The presence or absence of the CHM deletion was performed by PCR amplification of exons 7 to 11 that represented a 559 bp fragment from control cDNA and a 333-bp fragment from patient cDNA.

Western Blot Analysis

Cells were scraped into cold PBS containing Complete protease inhibitor cocktail tablets (Roche, Meylan, France) and centrifuged at 200 g for 5 min at 4° C. The pellet was resuspended in 2× Laemmli's sample buffer (Biorad, Marne La Coquette, France) containing Benzonase (Sigma Aldrich). The protein concentration of the lysates was measured using the Pierce BCA Protein Assay kit (ThermoFisher Scientific, Graffenstaden, France) and loaded onto an AnyKD precast MiniProtean TGX Stain Free gel (Biorad). The separated proteins were electrotransferred using a Trans-Blot® Turbo™ Mini PVDF Transfer Pack and System (Biorad). After blocking for 1 h in 0.5% Tween-PBS in 5% skim milk (blocking solution), the membrane was incubated with 1/1000 dilution in blocking solution of a monoclonal mouse anti-REP1 antibody (clone 2F1; Millipore, Saint Quentin en Yvelines, France) for 1 h at room temperature. After 3 washes in 0.5% Tween-PBS, the filter was incubated with 1/10 000 dilution of horseradish peroxidase (HRP)-conjugated sheep antibody against mouse whole immunoglobulins (Life Technologies). The detection step was performed using the Amersham ECL prime western blotting detection reagent (GE Healthcare).

Lentiviral Vector Production

Lentiviral-based plasmids containing the doxycycline-inducible transcription factors c-MYC (FUW-tetO-hMYC; plasmid ID 20723), SOX2 (FUW-tetO-SOX2; 20724), KLF4 (FUW-tetO-KLF4; 20725), OCT4 (FUW-tetO-OCT4; 20726), the reverse doxycycline transactivator M2rtTA (FUW-M2rtTA; 20342) and GFP (FUGW; 14883) were purchased from Addgene (Cambridge, Mass., USA). Lentiviral vectors were produced by the Lentiviral production platform (Montpellier, France). Infectious titre of FUGW was calculated at 1010 TU/ml. The infectious titres of the remaining viruses were estimated by performing a ratio of their P24 concentration with that of FUGW: FUW-tetO-hMYC—$2 \times 10^9$ TU/ml; FUW-tetO-SOX2—$7 \times 10^9$ TU/ml; FUW-tetO-KLF4—$8 \times 10^9$ TU/ml; FUW-tetO-OCT4—$3 \times 10^9$ TU/ml and FUW-M2rtTA –$9.8 \times 10^9$ TU/ml.

Feeder Cells

Newborn human foreskin fibroblasts were purchased from ATCC (hFF-1; LTC standards, France). Cells were cultivated in DMEM containing Glutamax (Gibco, Life technologies) supplemented with 10% FCS and irradiated by a dose of 35 Gray using a Cegelec BloodXrad irradiator (Etablissement Francais du Sang, Montpellier, France). Feeder cells were seeded at a density of $2.5 \times 10^5$ cells/35 mm plate.

Reprogramming and iPSc Culture

Prior to beginning reprogramming, the appropriate MOI for the transduction experiments was calculated using the GFP-encoding FUGW vector. CHM patient fibroblasts were then seeded in 6-well plates at a density of $10^5$ cells per well of a 6-well plate on day 0 in DMEM containing Glutamax supplemented with 10% FCS and 1% penicillinstreptomycin-amphotericin B. On day 1, cells were transduced with the 5 viruses (the control vector FUGW was not used for the reprogramming experiments) at an MOI of 10 per vector (total MOI of 50) in the presence of 8 µg/ml polybrene. On day 2, the cells were rinsed with PBS and fresh media added. On day 5, the media was renewed and supplemented with 2

μg/ml of doxycycline. On day 6, the transduced cells were dissociated with 0,25% trypsin (Gibco) and the cells from 1 well were divided over 4 wells containing feeder cell layers (1/4 dilution). The cells were cultured in ES media (KO DMEM (Gibco) supplemented with 20% KO serum replacement (Gibco), 200 mM L-glutamine (Gibco), 1% non-essential amino acids (Gibco), 0.1% B-mercaptoethanol (Gibco), 1% penicillin-streptomycin (Gibco) and 10 ng/ml ☐FGF (Peprotech, Neuilly Sur Seine, France) containing 2 μg/ml doxycycline (Sigma Aldrich) and the media changed daily. Resulting iPSc were mechanically passaged using a scalpel under a Lynx stereomicroscope (Vision Engineering SA, Le Plessis Pâté, France) onto 35 mm plates containing feeder cells in ES media.

Teratoma Formation and Analysis iPSc were pre-treated with 10 μM ROCK (Rho-associated coiled-coil forming protein serine/threonine kinase) inhibitor (Y-27632; Sigma Aldrich), for 1 hour at 37° C. and then enzymatically dissociated with 1× TrypLE Select (Gibco) for 10 min at 37° C. Dissociated cells were seeded at density of 5000 cells/cm$^2$ in a 10-cm plate containing a feeder cell layer and cultured in ES media containing ROCK inhibitor for 24-h post-passaging. Cells were enzymatically passaged 5 times prior to injection. Dissociated cells were resuspended in ES media containing 30% BD Matrigel Basement Membrane Matrix (BD Biosciences, Le Pont de Claix, France) at a concentration of 2×106 cells per 200 μl injected. Animal breeding and experiments were carried out in accordance with the European and National guidelines for the care and use of laboratory animals (Council Directive 2010/63/EU) and approved by institutional and regional ethics committees (permit number CEAA-LR-12157). NOD.Cg-Prkdcscid Il2rgtmlWjl/SzJ mice (Charles River, L'Arbresle, France) were anaesthetised with 35 mg/kg ketamine (Merial, Lyon, France) and 14 mg/kg xylazine (Bayer Healthcare, Loos, France), shaved on the left and right hind flanks, and injected subcutaneously with the 200 μl cell mixture using a 1 ml syringe attached to a 27-gauge needle. As controls, mice were injected with 30% Matrigel/ES media containing no cells or cells from previously characterised wild-type iPSc (M4C7; (Ramirez et al, 2013)). The mice were housed in individually ventilated cages and were euthanized when the tumours reached a maximum size of 1 cm2 (~2-mo post-injection). Tumours were dissected, rinsed in PBS and fixed in 3.7% formaldehyde and embedded in paraffin. Four μm sections were stained with haematoxylin-eosin and analysed for the presence of the three germ layers.

RPE Generation

To differentiate iPSc into RPE we used a previously described spontaneous differentiation protocole (Liao et al, 2010) with minor modifications. Briefly, iPSc colonies were allowed to grow to confluence on feeder cells and the ☐FGF was then removed from the ES media. The media continued to be changed daily during the differentiation process. Pigmented foci appeared over the course of the month following ☐FGF-depletion, which were manually dissected. The foci from one plate were pooled, dissociated with 0.25% trypsin, seeded onto 24-or 6-well culture dishes coated with Matrigel (diluted 1:30) and cultured in FGF-depleted ES media. Once a confluent monolayer was reached, the cells took on a pigmented polygonal morphology and could be kept in culture long-term. Cells were passaged by trypsin dissociation and amplified as required. All analyses were performed on RPE at the third passage (P3). Fluid-filled domes were observed SteREO Discovery V2.0 microscope (Carl Zeiss S.A.S, Le Pecq, France).

Electron Microscopy

RPE was passaged onto translucent BD Falcon cell culture inserts with high density 0.4 μM pores (BD Biosciences). When a characteristic morphology was reached, the filters were detached from the chambers, fixed in 3.3% glutaraldehyde, post-fixed in 2% osmium tetraoxide and embedded in epoxy resin. Semi-thin (700 nm) sections were stained with toluidine blue and observed under light microscopy. Seventy nm sections were stained with uranyl acetate and lead citrate and visualised using a Hitachi H7100 transmission electron microscope (Centre Regional d'Imagerie Cellulaire (CRIC), Montpellier, France).

Immunofluorescence Microscopy

For the immunofluorescence studies, iPSc and RPE were seeded onto plastic 96-well dishes whereas fibroblasts were seeded on glass coverslips. All cell types were fixed with 3.7% formaldehyde and blocked in 5% donkey serum/1% BSA. Cells were permeabilised with 0.2% Triton x-100 or 0.05% saponin. Primary antibodies were incubated on sections overnight at 4° C. and the secondary antibody incubated 45 min at room temperature with 0.2 μg/ml bisBenzimide Hoechst (Sigma-Aldrich) and 1 ng/ml phalloidin-TRITC (Sigma-Aldrich) prior to mounting in Dako Fluorescent Mounting Media (Dako France S.A.S., Les Ulis, France) when appropriate. For the iPSc, the primary antibodies used were 1:5 dilution rat IgM anti-human SSEA3 (Developmental Studies Hybridoma Bank, University of Iowa, Iowa City, Iowa, U.S.A.) and 1:10 goat anti-human NANOG (R&D Systems Europe, Lille, France). For the RPE, the primary antibodies used were 1:100 dilution rabbit anti-human ZO1 (Invitrogen, Life technologies), 1:250 rabbit anti-human MERTK (AbCam, Cambridge, Great Britain), 1/150 dilution mouse anti-human RPE65 (AbCam) and 1:1000 mouse antihuman CRALBP (directed against the recombinant protein; Agrobio, La Ferte St Aubin, France). For the fibroblasts, the primary antibody used was 1/500 dilution mouse anti-human REP1 (Millipore). For all, the secondary antibodies were 1:800 dilution donkey anti-mouse IgM-Alexa594 or -Alexa488 or 1:1000 dilution donkey anti-mouse, anti-rabbit or anti-goat IgG-Alexa Fluor 594 or -Alexa 488 (Molecular probes, Invitrogen). For the phagocytosis studies, cells were incubated with 1 μm in diameter, yellow-green (505/515 nm) carboxylatemodified microspheres (FluoSpheres; Molecular Probes, Life technologies) at a quantity of 160 beads per cell. Cells were observed using a Zeiss 5 live duo highspeed/spectral confocal microscope and image acquisition performed using the corresponding acquisition software (Carl Zeiss S.A.S.; Montpellier RIO Imaging platform).

Reverse Transcription and Quantitative PCR Studies

Quantitative RT-PCR (qPCR) was used to analyse the expression of the exogenous transgenes in the transduced fibroblasts as well as the silencing of the exogenous transgenes and the activation of the endogenous pluripotency genes in the iPSc. Following RNA isolation and cDNA synthesis, qPCR amplification was performed using gene-specific primers (Supplementary Material, Table) and the LightCycler® 480 SYBR Green I Master mix on a LightCycler® 480 II thermal cycler (Roche). Gene expression was normalised to GAPDH expression. Results were analysed using LightCycler® 480 software and Microsoft Excel. The expression of RPE-specific markers was analysed using classic RT-PCR amplification with gene-specific primers and the amplification products were analysed on 2% agarose gel.

In Vitro Prenylation Assay

RPE cultured in a well of a 24-well plate was washed in cold PBS, scraped in PBS containing anti-proteases, pelleted and resuspended in cold, degased prenylation/lysis buffer prepared fresh as described previously (Wu et al, 2007). Cells were incubated 15 minutes on ice and then sonicated 3 times 45 seconds at 40 Hertz. The cells were then centrifuged 5 min at 1500 g at 4° C., the supernatant collected and further centrifuged 30 min at 450 000 g at 4° C. on an Optima MAX-TL ultracentrifuge (Beckman, Villepinte Roissy, France). An in vitro prenylation assay was performed on the freshly prepared lysate using 5 µM biotin-labelled geranyl pyrophosphate (B-GPP) (Euromedex, Souffelweyersheim, France) as a prenyl group donor, 0.5 µM recombinant REP1 (Euromedex), 0.5 µM Rab geranylgeranyl transferase (RGGT; Euromedex) and 20 µM GDP in prenylation/lysis buffer at 37° C. for 1 h (Nguyen et al, 2010; Wu et al, 2007). The prenylation reaction was quenched with 6× SDS, boiled at 90° C. for 5 min and analysed by western blot. The membrane was incubated with 1:5000 HRP-conjugated streptavidin (Jackson ImmunoResearch, Cambridge, Great Britain) or 1:50 000 mouse anti β-Actin (Sigma Aldrich). Detection was performed using the Chemi-Doc MP Imaging system (Biorad) and the extent of biotin-geranyl incorporation quantified by scanning densitometry using the appropriate software package (Image Lab, Biorad) and expressed as a function of the beta-actin signal. To allow relative comparisons, the amount of biotin incorporation in CHM RPE was set to 100%.

Differential Centrifugation

Pelleted RPE cells from a well of a 24-well plate were thoroughly homogenised in 3 volumes of Subcellular Fraction Lysis Buffer (SFLB) containing 50 mM Tris-HCl (pH 7.5), 150 mM NaCl, 2 mM MgCl2, 0.5 mM EGTA, 0.5 mM EDTA, 5 mM DTT, 0.1 mM GDP and protein inhibitors as described (Seabra et al, 1995). The homogenate was centrifuged at 800×g at 4° C., the pellet discarded, and the supernatant ultracentrifuged at 450 000×g for 1 h at 4° C. to obtain the cytosolic and membrane fractions. Following ultracentrifugation, the pellet was resuspended in 1 volume of SFLB adjusted to 1% Nonidet P-40 (Sigma Aldrich). The protein content of the cytosolic supernatant and 1% Nonidet P-40-solubilized membrane fraction were analysed by western blot analysis. The membranes were incubated with 1:250 mouse anti-Rab27A (AbCam) or 1:50 000 mouse anti-β-Actin antibodies. The cytosolic and membrane levels Rab27A were quantified relative to the beta-actin loading control and expressed as a percentage of total Rab27A content for each well.

AAV Vector Production

The Viral Vector Production Platform, Nantes, France, produced all the AAV vectors used for this work. Briefly, the viral vectors were produced by transient transfection of 293 cells and the viral particles were either precipitated from the supernatant using PEG or, in the case of the AAV2/4 and-2/5 vectors, from the cell pellet using ammonium sulphate. The vectors were purified by double CsCl centrifugation, dialysed and titred by dot blot assay. For the transduction efficiency experiments, the titres of the AAV vectors expressing EGFP under control of the CMV promoter were as follows: AAV2/2-CMV-EGFP—$3.5 \times 10^{12}$ vector genomes (vg)/ml; AAV2/4-CMV-EGFP (provided by the intermediate of Dr. F. Rolling, Inserm UMR 1089, Nantes)—$3 \times 10^{11}$ vg/ml; AAV2/5-CMV-EGFP—$3.3 \times 10^{12}$ vg/ml; AAV2/8-CMV-EGFP—$9 \times 10^{12}$ vg/ml, and AAV2/9-CMV-EGFP—$2.55 \times 10^{12}$ vg/ml. For the proof of concept experiments, AAV plasmids carrying either the CHM gene (provided by Pr. J. Bennett, University of Pennsylvania, Pa., USA) or the EGFP gene (provided by the Nantes Viral Vector Production Platform) under the control of the CAG (chicken beta actin promoter with CMV enhancer) promoter were used to produce the following vectors: AAV2/5-CAG-CHM—$4.4 \times 10^{12}$ vg/ml and AAV2/5-CAG-EGFP—$2.34 \times 10^{12}$ vg/ml.

In Vitro AAV Transduction

For the transduction efficiency experiments, the iPSc-derived RPE was seeded in 96-well plates and 2×10 cells per well was estimated at confluence. Cells were transduced with 25 000 vg (dictated by the serotype with the lowest titre) in a minimum volume (50 µl) of □FGF-depleted ES media for 6 h to promote vector-cell interaction. The wells were then supplemented with extra media and the media changed every 3 to 4 days. At the desired timepoints, cells were dissociated with 0.25% trypsin, fixed in 3.7% formaldehyde and the number of EGFP-expressing cells analysed using a BD FACSCalibur flow cytometer (BD Biosciences) at 48-h, 1-, 2-, 4-and 6-wk post-transduction. Experiments were performed in duplicate. For transgene expression experiments, $2 \times 10^4$ fibroblasts were seeded in 24-well plates containing coverslips. Twenty-four h post-seeding cells were transduced with AAV2/5-CAG-CHM with 100 000 vg for 48 h. In parallel, wells without coverslips were transduced with AAV2/5-CHM-EGFP at an equivalent MOI for flow cytometry analysis. For the proof-of-concept experiments, iPSc-derived RPE was seeded in 24-well plates and $1.2 \times 10^6$ cells were estimated at confluence. Cells were transduced at an MOI of 100 000 and prenylation assays were performed at 4-wk posttransduction. Experiments were performed in triplicate.

Subretinal Injections

Eight week-old C57BL/6J male mice (Harlan France SARL, Gannat, France) were anesthetised with 70 mg/kg Ketamine and 28 mg/kg Xylasine and the pupils dilated by a drop of 0.5% tropicamide (Mydriaticum, Théa, France) in each eye. The cornea was covered with a drop of Lacryvisc (Alcon, Rueil-Malmaison, France) and a glass coverslip. Under a surgical microscope, the eye was first pierced at the corneal-scleral junction. Subsequently, subretinal injections were performed using a 5 µl Hamilton syringe and a bevelled 34 G needle. The eyes were injected with either 2 µl of PBS or 2 µl containing $4.68 \times 10^9$ vg of either AAV2/5-CAG-CHM or AAV2/5-CAG-EGFP. The eyes were followed at regular intervals by funduscopy (2-, 4-, 6-and 8-wk post-injection. At each timepoint, mice were anaesthetised, pupils dilated, and fundus photographs were taken using a Micron III Retinal Imaging Microscope (Phoenix Research Laboratories, Peasanton, Calif., USA). Electroretinogram studies were performed prior to sacrifice as previously described (Chekroud et al, 2011). Statistical comparisons performed using a Kruskall Wallis ANOVA and post-hoc comparisons were made using a Siegel-Castellan 2×2 comparison (Siegel & Castellan, 1988).

Analysis of Transgene Expression

Mice were sacrificed at 2-wk post-injection, the eyes were enucleated, and the anterior segment of the ocular globe was removed. For western blot analysis, the neuroretina was dissected and placed in lysis buffer (50 mM Tris pH 6.8, 10% glycerol and 2% SDS), respectively. Subsequently the RPE and choroid were scraped using a forceps in lysis buffer and pooled with the neuroretina. A percentage (7.5%) of the total protein sample was migrated, transferred and hybridised with anti-REP1 or 1/2000 dilution of rabbit anti-EGFP serum (Molecular probes, Invitrogen) as described above. For q-PCR analysis, the neuroretina and RPE/choroid samples were snap frozen prior to RNA isolation and cDNA synthesis. Q-PCR analysis was performed using gene specific primers normalised to L27 gene expression.

Histological Analysis

To assay EGFP expression, the eyes were enucleated and fixed in 3.7% formaldehyde for 6 h at 4° C., incubated in successive baths of 10%, 20%, 30% and 40% sucrose, prior to embedding in OCT matrix and sectioning at 14 µM (Reseau d'Histologie Expérimentale de Montpellier (RHEM)). To assay histology, the eyes were enucleated and fixed in 3.7% formaldehyde for 24 h at 4° C., dehydrated in serial ethanol baths, embedded in paraffin and sectioned at 4 µm (RHEM). For photoreceptor counting, sections were stained with haematoxylin and eosin. Microscopic images were acquired on a Slide Scanner (Hamamatsu Photonics K.K., Japan; Montpellier RIO Imaging platform). At least four sagittal sections per retina were counted (injection status masked) and the number of photoreceptor nuclei averaged.

Results

Characterisation of Patient Mutation

The characterisation of the genomic DNA from fibroblasts of patient CHM1 revealed a duplication of a 7-bp (TAGTTCT) (SEQ ID NO:3) sequence in intron 7 situated 40-bp upstream to the start of exon 8. In between the duplicated sequence was a 4-bp insertion (GATT) (SEQ ID NO:4). This first duplication was followed by a second duplication of a 15-bp sequence within exon 8 (GTCATGCATTCAATT) (SEQ ID NO:5) situated 68-bp after the start. The 97-bp DNA sequence situated between the two duplications, which comprised the end of intron 7 and the beginning of exon 8, were deleted. The loss of the intron 7 acceptor splice site and subsequent deletion of exon 8 resulted in a predicted frameshift at amino acid position 314 and a premature stop codon at position 332 (wild-type REP1 is 653 aa) truncating the second GDP dissociation inhibitor (GDI) domain of REP1. Western blot analysis with an antibody directed to an N-terminal epitope present in both wild-type and truncated REP1 (73.49 kDa), as well as in REP2 (74.08 kDa), detected 2 bands for the control cells and one band for the CHM cells (corresponding to REP2), showing that the truncated protein was unstable. Western blot analysis using a second REP1 specific antibody did not detect a protein in CHM1 cells as opposed to control cells.

Thus, the mutation carried by patient CHM1 abolished REP1 protein production. Moreover, the detection tests developed at the DNA, RNA and protein levels will serve to verify the presence of the patient's mutation in any cell type generated thereafter.

Generation and Validation of Patient-Specific iPS Cells

We used doxycycline-inducible lentiviral vectors carrying the Yamanaka transcription factor cocktail (c-MYC, KLF4, OCT4, SOX2) for the reprogrammation of CHM1 fibroblasts. We verified the expression of each transgene 24-h post-doxycycline induction by qPCR studies. One-week post-doxycycline induction, the fibroblasts began to change morphology with partially reprogrammed colonies (pre-iPSc colonies) appearing and disappearing over time. In contrast, 5-wk post-doxycycline induction, a morphologically characteristic colony was detected, which survived mechanical passaging into ES media without doxycycline. PCR amplification of CHM1 iPSc DNA showed that the original CHM deletion was present and that it led to the complete deletion of exon 8 from the mRNA as evidenced by a difference of 226 by between the cDNA fragments generated from wild-type and CHM1 iPSc RNA. Moreover, the CHM1 iPSc did not present any large chromosomal anomalies that may occur during reprogramming as shown by karyotype analysis.

The pluripotence of the CHM1 iPSc was verified by a variety of techniques and using a wild-type clone M4C7 (Ramirez et al, 2013) as a positive control. Firstly, at the mRNA level, qPCR studies demonstrated the silencing of exogenous c-MYC, KLF4, OCT4 and SOX2 and the activation of expression of endogenous OCT4, SOX2, LIN28 and NANOG in the CHM1 iPSc. Secondly, alkaline phosphatase staining was positive and immunofluorescence (IF) studies confirmed the expression of NANOG and indicated the expression of SSEA3. Lastly the CHM1 iPSc induced the formation of teratomas when injected subcutaneously in immuno-deficient mice and the expression of markers of the three germ layers was confirmed by histological analysis: ectoderm, mesoderm and endoderm.

In conclusion, we generated bona fide iPSc of a CHM patient.

Generation and Validation of Patient-Specific RPE

We used a spontaneous differentiation protocol to generate retinal pigment epithelium (RPE) from wild-type M4C7 and CHM1 iPSc. Approximately 30 d after the iPSc were cultured to confluence and bFGF removed from the media, pigmented foci appeared in the plates. These foci were mechanically passaged and at confluence gave rise to a layer of polygonal pigmented cells characteristic of RPE. Seeding the cells on translucent porous filters allowed sectioning and histological analysis. Observation of semi-thin sections demonstrated that cell layer was a regular monolayer. Transmission electron microscopy showed that the monolayer was a polarised epithelium with microvilli on the apical side, a nucleus on the basal side, cytosolic melanosomes and desmosomes indicative of tight junctions. The epithelium appeared to secrete a basal lamina detectable between the RPE cells and the matrigel coating. RT-PCR studies demonstrated that the iPSc-derived epithelium expressed classic genes for the visual cycle (such as RLBP1, RPE65, LRAT, RDH5), retinal development (PAX6), phagocytosis (MERTK), pigmentation (TYR), ion transport (BEST1), and cell adhesion (ZO-1). Furthermore, IF studies showed that MERTK was localised in the apical microvilli (FIG. 4F), CRALBP and RPE65 in the cytoplasm, and ZO-1 at the apical junctions in accordance with their respective roles. Moreover, the presence of desmosomes was consistent with the positive ZO-1-labelling. In addition to this classic RPE morphology, two of the in vivo functions were also conserved in the iPSc-derived RPE. Firstly, over time, fluid-filled domes of varying sizes appeared in the plates. These were likely formed due to apico-basal fluid transport lifting the RPE off the culture plate. Secondly, the RPE was able to phagocytose FluoSpheres, which could be detected by epifluorescence microscopy. FACS analysis showed that quantity of spheres internalised increased over time. Finally, the original CHM mutation was present at the DNA and RNA level, and REP1 was absent from the CHM1 RPE.

Taken together, these results confirmed that this iPSc-derived epithelium from both wild-type and CHM1 iPSc was bona fide and functional RPE.

Detection Biochemical Defect

In order to determine whether the iPSc-derived RPE from individual CHM1 reproduced the biochemical defect of patients, we set up two different techniques to assay the prenylation status of intracellular Rabs, a reflection of the activity of REP1. Firstly, we assayed the size of the unprenylated Rab pool in the cells using an in vitro prenylation assay. To this end, we added recombinant RGGT, REP1, and biotinylated prenyl donor to the lysate of wild-type and CHM1 cells, Thus, if an unprenylated Rab pool were available for prenylation, the integrated biotin could be detected by western blot analysis using HRPconjugated streptavidin. The detected bands corresponding to biotinylated Rabs were normalised according to the □-actin loading control and the prenylated Rab pool detected in the CHM1 RPE was set at 100% to allow relative comparisons. On average, an ~4-fold lower level of biotinylated Rab proteins was detected in the wild-type RPE, consistent with the fact that, in the presence of REP1 and REP2, most Rabs are prenylated and membrane-bound. Secondly, we specifically assayed the subcellular distribution of Rab27A, a Rab protein highly expressed in the retina (Seabra et al, 1995). By differential centrifugation, we separated the cytosolic and membrane fractions of wild-type and CHM1 cell lysates and analysed the respective content of Rab27A by western blot analysis with a specific antibody. As for the prenylation assay, the amount of Rab27A in each fraction was normalised according to the beta-actin loading control. Subsequently, the total amount (cytosolic+membrane) of Rab27A in each cell lysate was set at 100% and the amount in each fraction was expressed as a percentage of total Rab27A content. In wild-type cells, the amount of cytosolic Rab27A was on average ~4.7-fold lower than the amount that was membranebound. In contrast, in CHM1 RPE, the amount of cytosolic Rab27A was on average ~2-fold higher than that observed in wild-type cells and ~1.8-fold lower than the amount that was membrane-bound.

Thus, in conclusion, the CHM1 RPE cells mimicked the biochemical difference seen in CHM patients, i.e. an underprenylation of Rab proteins due to the absence of REP1.

Transduction RPE

To determine whether we could transduce the iPSc-derived RPE with AAV vectors and to ascertain the most efficient serotype, we tested a panel of vectors expressing EGFP under the control of a CMV promoter: AAV2/2, -2/4, -2/5, -2/8 and -2/9. Firstly, all serotypes were able to transduce the iPSc-derived RPE as determined by EGFP expression and the efficiency of transduction was dose-dependent. Secondly, for an equivalent quantity of viral genomes, the efficiency of each serotype was 2/5>2/2>2/4>2/8/>2/9 (FIG. 1a). Notably, on average, AAV2/5 vector expression was 1.5-fold higher than that of AAV2/2 (1.45±0.26, n=5) and it was approximately 6-old higher than both AAV2/8 and 2/9. To explore a dose-dependent effect of these four serotypes, we increased the number of viral genomes per cell to 100 000.

Figure 1B:
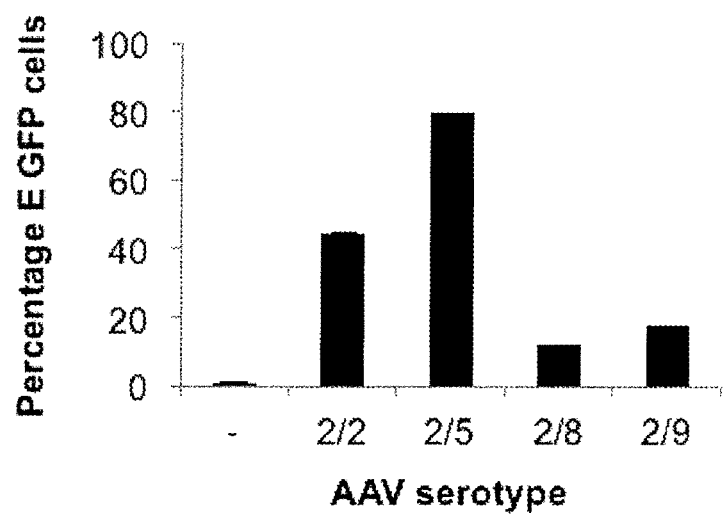
Figure 1C:
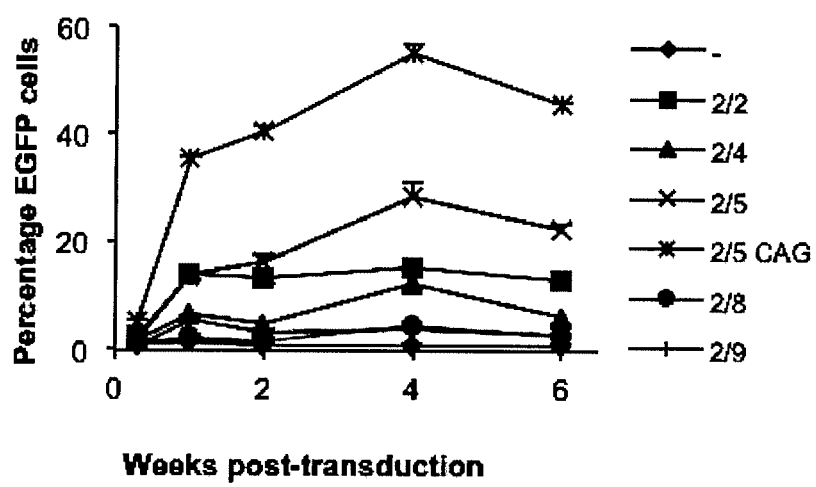
Figure 1D:
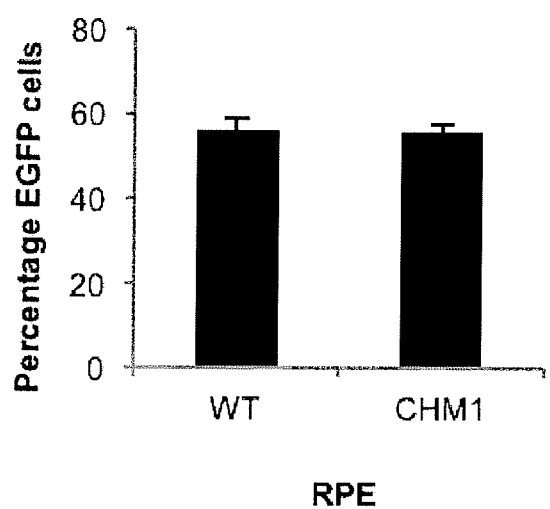

Although the transduction efficiency of AAV2/5 increased from 55 to 80% of cells EGFP positive, the transduction of efficiency of AAV2/2 and AAV2/8 or 2/9 remained approximately 1.5- and 6-fold lower, respectively (FIG. 1b). In addition, we used the most efficient serotype (AAV2/5) to compare the efficacy of two different promoters: CMV versus CAG (chicken beta-actin with a CMV enhancer). On average, CAG directed a 2-fold higher level of expression than CMV (2.04 ±0.21, n=5; FIG. 1a). Thirdly, a time-course experiment suggested that expression peaked at 4-wk post-transduction (FIG. 1c). Lastly, the genotype of the iPSc-derived RPE (i.e. wild-type vs. CHM) did not influence transduction efficiency (FIG. 1d).

Taken together, these results demonstrated that AAV2/5 vectors transduce human iPSc-derived RPE better than other serotypes, notably AAV2/2 and AAV2/8.

AAV2/5-CAG-CHM-Directed REP1 Expression

Figures 2A, 2B, 2C:
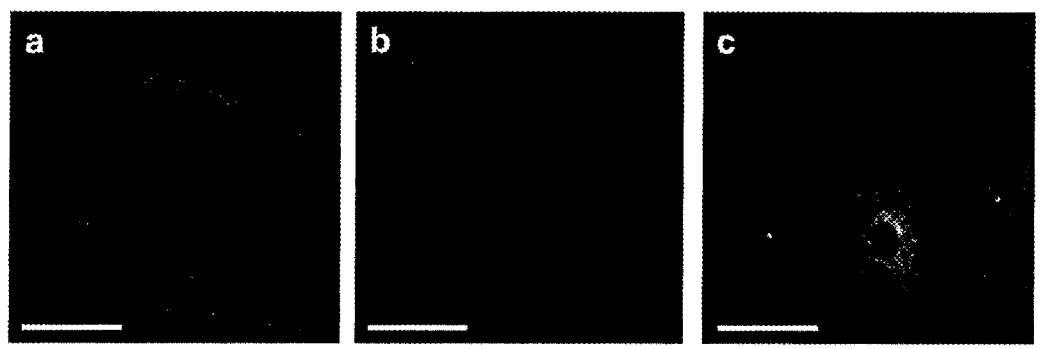
Figures 2D, 2E:
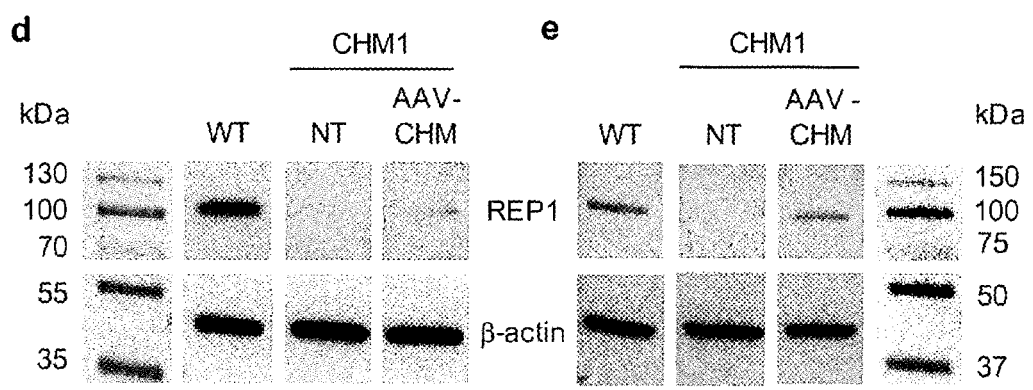

We thus generated an AAV2/5 vector expressing CHM under control of the CAG promoter. IF studies of CHM1 fibroblasts transduced with AAV2/5-CAG-CHM confirmed that the encoded REP1 was expressed and correctly localised as a mostly vesicular staining in the cytoplasm (FIG. 2a-c). Western blot analysis of transduced fibroblasts (FIG. 2d), followed by semi-quantification of REP1 expression normalised to beta-actin levels, indicated that REP1 expression was equivalent to ~17% of wild-type. In parallel, and in accordance with the western blot data, we transduced fibroblasts with AAV2/5-CAG-EGFP and detected 14% of EGFP-positive cells by flow cytometry. Consistently, initial transduction experiments of RPE with AAV2/5-CAG-CHM, followed by western blot (FIG. 2e) and semi-quantification analyses, indicated that REP1 expression was equivalent to 53% of wild-type for 40% of EGFP-positive cells (as determined by flow cytometry of AAV2/5-CAG-EGFP-transduced RPE cells).

Thus, taken together, these data show that REP1 expression in CHM1 cells transduced with AAV2/5-CAG-CHM was at least equivalent to that of wild-type.

CHM Gene Transfer

Figures 3A, 3B, 3C, 3D:
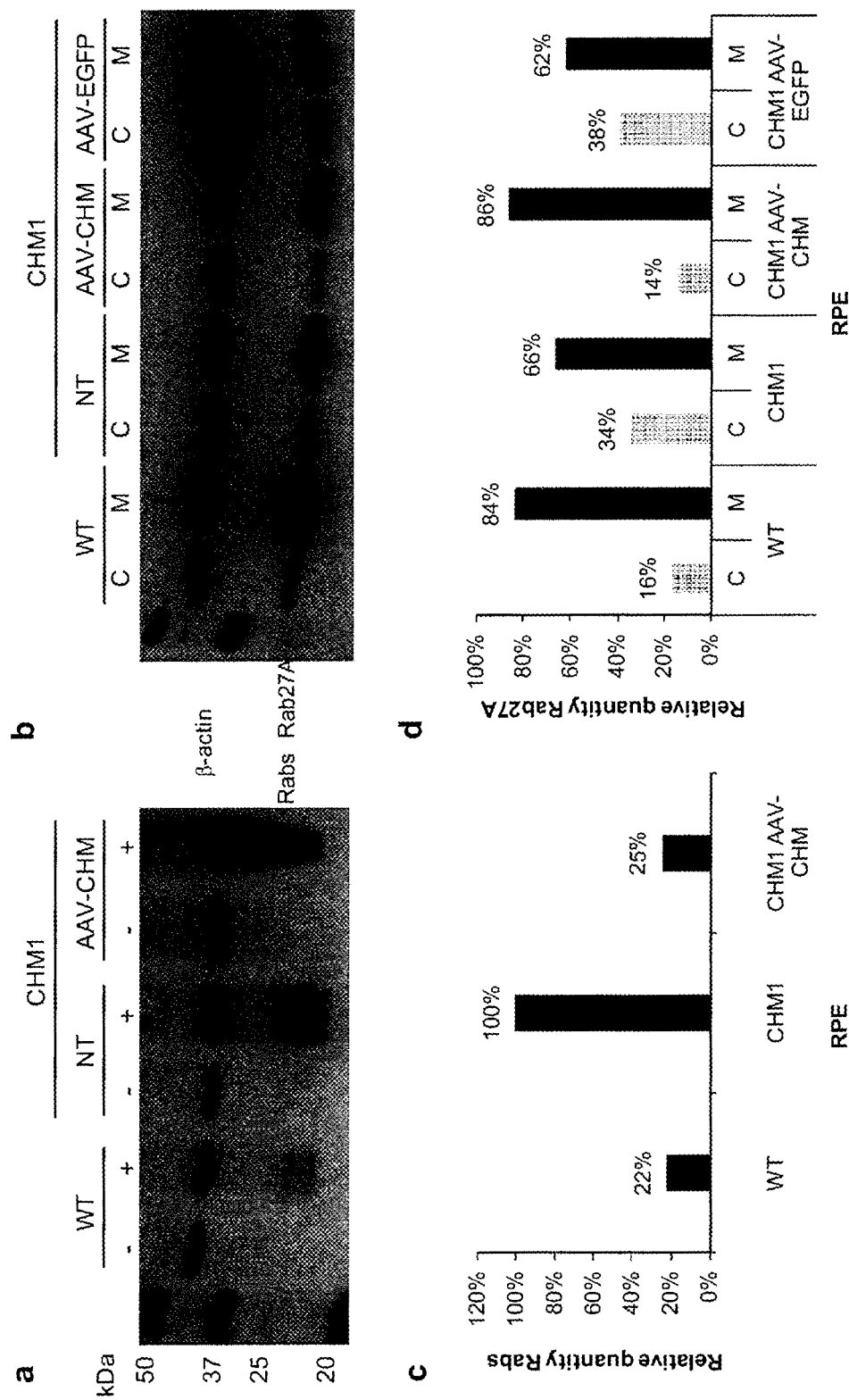

CHM1 RPE was then transduced with AAV2/5-CAG-CHM vector and, based on the results of the time-course experiments, REP1 activity was analysed 4-wk post-transduction. A representative experiment is shown in FIG. 3a. As above, in the prenylation experiment, the detected pool of biotinylated Rabs was set at 100%. Following transduction of the CHM1 RPE with the AAV2/5-CAG-CHM vector, there was a 4.5-fold reduction in the quantity of biotinylated Rab proteins, which was equivalent to levels in the wild-type RPE (FIG. 3c). Similarly, an analysis of the subcellular distribution of Rab27A following AAV2/5-CAG CHM transduction (FIG. 3b), showed that the cytosolic fraction of Rab27A was reduced 2.4-fold, and the membrane-bound fraction increased 1.3-fold, compared to non-transduced RPE, which was equivalent to the levels in the wild-type RPE (FIG. 3d). Moreover, transduction of CHM1 RPE with a control AAV2/5-CAG-EGFP vector did not dramatically alter the proportions of Rab27A in each fraction.

In conclusion, we provided the proof-of-concept that AAV2/5-mediated CHM gene transfer restores a normal cellular phenotype in RPE of CHM patients.

In Vivo Gene Transfer

Figure 4A:
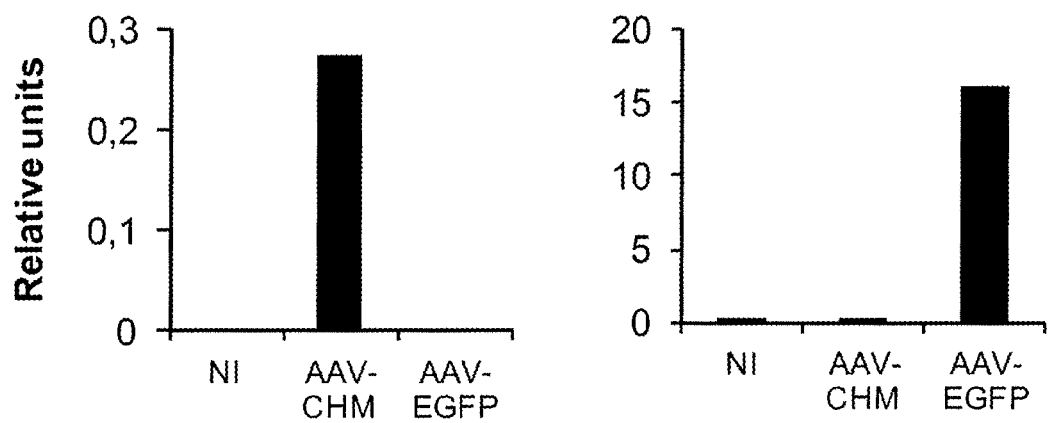
Figure 4B:
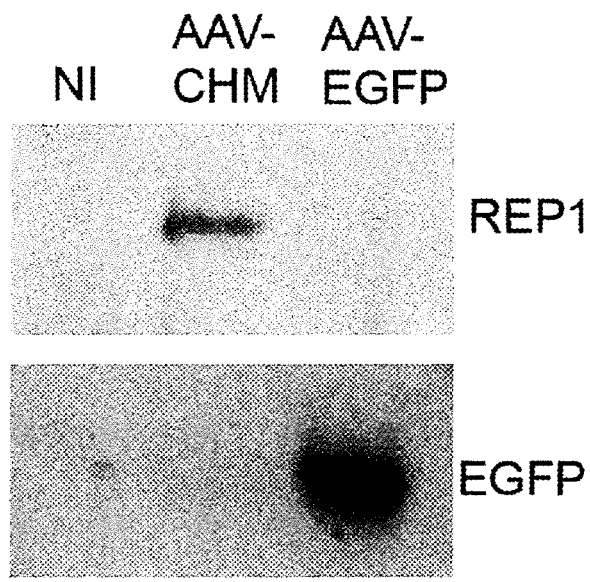
Figure 4C:
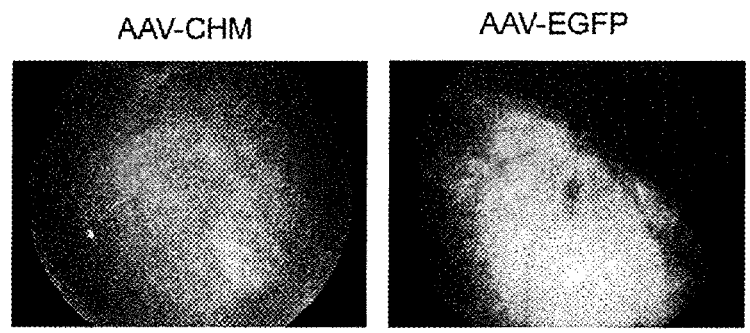
Figure 4D:
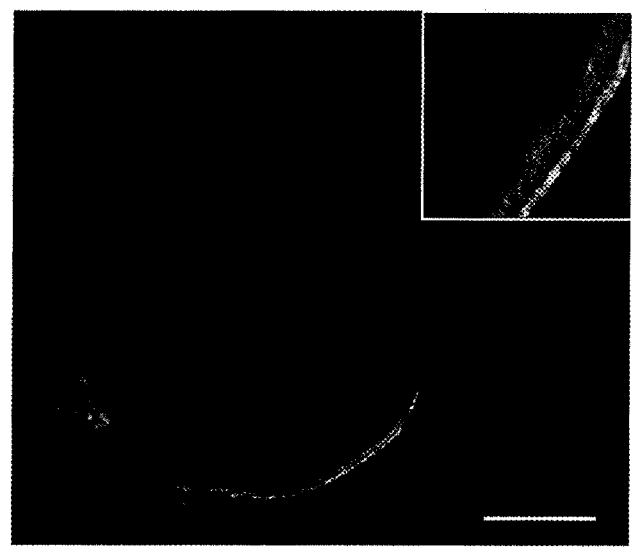

In order to complement these in vitro studies, we injected mouse eyes with PBS, AAV2/5-CAG-EGFP or AAV2/5-CAG-CHM and assayed for expression. As early as 3-d post-injection, EGFP expression was lightly perceptible in the fundus of mice injected with AAV-CAG-EGFP. Q-PCR studies performed on the retinal extracts 2-wk postinjection showed the specific expression of human CHM in the retinal extracts of AAV2/5CAG-CHM-injected mice and of EGFP in the CAV2/5-CAG-EGFP-injected eyes (FIG. 4a). Western blot analysis at the same timepoint confirmed this specific expression at the protein level (FIG. 4b). We followed the evolution of EGFP expression by funduscopy at 1-wk, 2-wks (FIG. 4c) and 1-mo post-injection, and detected widespread transduction, which appeared stable. Fluorescence microscopy confirmed transduction of half of the retina up to the optic nerve and EGFP expression was detected in both the RPE and photoreceptors (FIG. 4d).

In conclusion, AAV2/5-mediated gene transfer in vivo in the mouse retina results in gene expression in both the RPE and in photoreceptors.

Discussion:

Stem cells have revolutionised the field of human cell culture as they represent an immortal propagation of pluripotent cells that theoretically can generate into any cell type in the body (Yu & Thomson, 2008). In particular, induced pluripotent stem cells (iPSc) represent an exceptional tool as they can be generated from adult somatic cells (Takahashi et al, 2007; Yu et al, 2007) hence circumventing the ethical considerations involved with the use of human embryonic stem (ES) cells. Furthermore, as stem cells can theoretically differentiate into any cell type of the body, they allow access to primary cell types that could not have been isolated by conventional techniques (Grimm, 2004). Moreover, if the starting material comes from an individual with a particular genetic disease, the targeted cell type could then represent a disease-specific cellular model (Park et al, 2008).

We have used the iPSc technique to generate a disease-specific retinal pigment epithelium (RPE) model with which we were able to provide a proof-of-concept for a gene therapy approach. This is the first example of such a strategy. Generally, iPSc-derived cell models are used to further understand the pathophysiology of the disease (Singh et al, 2013), for screening the efficiency of pharmacological drugs (Egawa et al, 2012), or for generating cell precursors in view of cell transplantation (Tucker et al, 2011). We show here the further potential of an iPSc-derived model for testing the efficiency of a gene replacement strategy in the cell type that would be targeted in a corresponding therapeutic trial.

AAV vectors are now widely accepted as safe and efficient for retinal gene therapy. Of the various AAV serotypes identified, AAV2/2, -2/4, -2/5, -2/8 and -2/9 have all been shown transduce retina cell types at variable efficiency depending on the species (Vandenberghe & Auricchio, 2012). All five of these serotypes transduce the RPE, whereas all except AAV2/4 transduce photoreceptors (Weber et al, 2003). Furthermore, concerning photoreceptor transduction, it has been shown in the mouse and pig eye that AAV2/5, -2/8 and -2/9 show greater efficiency than AAV2/2 (Allocca et al, 2007; Mussolino et al, 2011). In humans to date, two serotypes, AAV2/2 (Bainbridge et al, 2008; Hauswirth et al, 2008; Maguire et al, 2008) and -2/4 (unpublished), have been tested and the accruing toxicology data suggest that these vectors are safe for the human eye, however the most efficient vector remains to be ascertained.

We assayed transduction efficiency of the aforementioned AAV serotypes in iPSc-derived human RPE. Consistent with the literature, AAV2/5 resulted in a 2-fold higher expression level for the same promoter than AAV2/2. However, we showed that unexpectedly AAV2/8 was lower than that observed with AAV2/2. We initially thought that this was because the first stock of AAV2/8 that we used was produced by a different vector production platform than the other serotypes. Thus, we obtained a second stock from the same production platform but the results were identical. Moreover, we explored a dose-dependent effect, but AAV2/5 was consistently more effective than AAV2/8 in the human RPE. Furthermore, the results were similar for AAV2/9. It is possible that this this is due to a difference in cell surface receptors as AAV2/5 binds either alpha-2-3 N-linked sialic acids whereas AAV2/2, 2/8 and 2/9 do not use this receptor (for review see (Agbandje-McKenna & Kleinschmidt, 2011). As we have shown that the human iPSc-derived RPE cells features the classical properties of a functional in vivo RPE, the superiority of AAV2/5 over AAV2/8 and AAV2/9 at all doses observed in vitro must also apply in vivo. Thus, it is likely that in the human RPE, a lower dose of an AAV2/5 viral vector will provide superior transduction compared to other serotypes, which has important safety implications.

We showed that AAV2/5 transduction of the RPE is dose-dependent and that by using a CAG promoter as opposed to a CMV promoter, transduction efficiency could be further increased. We reached transduction efficiencies up to 85%, which was surprising if we consider the notorious difficulties of using AAV vectors for in vitro transduction. Transduction was likely aided by the phagocytic properties of the RPE, which represent one of its key roles in the eye (Sparrow et al, 2010). In vivo, the photoreceptors continuously renew their outer segment disks and shed their old segments at the RPE-side daily. The RPE is responsible for the phagocytosis of the shed disks, which would be toxic if they accumulated. Thus, the phagocytosis ability of the iPSc-derived RPE mimics the situation encountered by AAV vectors administered into the subretinal space and further highlights the exceptional potential of this model. In vivo, the photoreceptors continuously renew their outer segment disks at the apical side and thus daily shed their old segments at their base. The RPE is responsible for the phagocytosis of the shed disks, which would be toxic if they accumulated. This property may also explain the higher transduction efficiency of the RPE as compared to that of photoreceptors with AAV vectors in all species (Vandenberghe et al, 2011). Lastly, once the RPE is confluent in culture cell division stops, therefore making it possible to follow transgene expression over the long-term as the AAV vector is not lost over time.

In order to determine whether we could use a cellular model of the human RPE for testing the efficiency of an AAV2/5-mediated gene transfer approach, we generated iPSc-derived RPE from fibroblasts of an individual with choroideremia. Choroideremia is a retinal dystrophy in which the degradation of the RPE appears to play a key role in its pathophysiology (Krock et al, 2007; Tolmachova et al, 2010). Furthermore, it is a perfect candidate for an iPSc-derived approach because there does not exist a disease-specific animal model that is informative for gene rescue studies (Tolmachova et al, 2013; Tolmachova et al, 2012). We show here that choroideremia-specific RPE expresses characteristic proteins, is functional, and mimics the biochemical defect seen in patients: the absence of the encoded protein, REP1, results in an underprenylation of Rab proteins, notably Rab27A, leading to a decreased number of membrane-associated Rabs and an increased cytosolic pool. This provided a quantitative read-out with which to evaluate restoration of function. Using two independent assays, we showed that CHM gene transfer was able to reduce the pool of cytosolic Rabs in general, and Rab27A specifically. This provides the proof-of-concept in human RPE that AAV2/5-mediated CHM gene transfer could restore a normal cellular phenotype The work described herein demonstrates the possibility of using a human disease-specific cellular model for proof-of-concept studies in the absence of an appropriate animal model. This has been aided by the fact that the vehicle itself (albeit a different serotype) has already been validated by clinical trials targeting the retina, thus the in vitro study has mainly evaluated the functionality of the transgene. If the field of AAV-mediated retinal gene therapy continues to advance positively, then this same strategy could be applied to numerous IRDs in which the RPE is affected, hence facilitating clinical translation.

Our approach of providing a proof-of-concept in a pertinent human cellular model of the diseased retina is the first example of its kind and has revolutionised <<pre-clinical>> thinking. Two other articles confirming the difficulty of using the conditional mouse models for restoration of phenotype studies for choroideremia and providing proof-of-concept essentially on cellular models (CHM fibroblasts and iPSc) have been published (Tolmachova et al, 2013; Vasireddy et al, 2013). Here, we go a step further and provide the proof of concept in the RPE cells, the principal cell type affected, hence avoiding extrapolation from cell types not implicated in disease pathogenesis. Furthermore, these aforementioned papers assessed the efficiency of AAV2/2-mediated CHM gene therapy, which we show is less efficient than AAV2/5 in the human RPE.

To conclude these data provide the demonstration for the first time that an AAV2/5 vector, which we used to vehicle the CHM gene under the control of the CAG promoter, is a better vector for gene therapy on human RPE cells of patients with choroideremia than AAV2/2, AAV2/4, AAV2/8 and AAV2/9 vectors.

REFERENCES

Throughout this application, various references describe the state of the art to which this invention pertains. The disclosures of these references are hereby incorporated by reference into the present disclosure.

Agbandje-McKenna M, Kleinschmidt J (2011) AAV capsid structure and cell interactions. *Methods Mol Biol* 807: 47-92

Allocca M, Mussolino C, Garcia-Hoyos M, Sanges D, Iodice C, Petrillo M, Vandenberghe L H, Wilson J M, Marigo V, Surace E M, Auricchio A (2007) Novel adeno-associated virus serotypes efficiently transduce murine photoreceptors. *J Virol* 81: 11372-11380

Bainbridge J W, Smith A J, Barker S S, Robbie S, Henderson R, Balaggan K, Viswanathan A, Holder G E, Stockman A, Tyler N, Petersen-Jones S, Bhattacharya S S, Thrasher A J, Fitzke F W, Carter B J, Rubin G S, Moore A T, Ali R R (2008) Effect of gene therapy on visual function in Leber's congenital amaurosis. *N Engl J Med* 358: 2231-2239

Bennett J, Ashtari M, Wellman J, Marshall K A, Cyckowski L L, Chung D C, McCague S, Pierce E A, Chen Y, Bennicelli J L, Zhu X, Ying G S, Sun J, Wright J F, Auricchio A, Simonelli F, Shindler K S, Mingozzi F, High K A, Maguire A M (2012) AAV2 gene therapy readministration in three adults with congenital blindness. *Science translational medicine* 4: 120ra115

Berger W, Kloeckener-Gruissem B, Neidhardt J (2010) The molecular basis of human retinal and vitreoretinal diseases. *Prog Retin Eye Res* 29: 335-375

Bocquet B, Lacroux A, Surget M O, Baudoin C, Marquette V, Manes G, Hebrard M, Senechal A, Delettre C, Roux A F, Claustres M, Dhaenens C M, Rozet J M, Perrault I, Bonnefont J P, Kaplan J, Dollfus H, Amati-Bonneau P, Bonneau D, Reynier P, Audo I, Zeitz C, Sahel J A, Paquis-Flucklinger V, Calvas P, Arveiler B, Kohl S, Wissinger B, Blanchet C, Meunier I, Hamel C P (2013) Relative frequencies of inherited retinal dystrophies and optic neuropathies in Southern France: assessment of 21-year data management. *Ophthalmic epidemiology* 20: 13-25

Chekroud K, Arndt C, Basset D, Hamel C P, Brabet P, Pequignot M O (2011) Simple and efficient: validation of a cotton wick electrode for animal electroretinography. *Ophthalmic research* 45: 174-179

Colella P, Cotugno G, Auricchio A (2009) Ocular gene therapy: current progress and future prospects. *Trends Mol Med* 15: 23-31

Egawa N, Kitaoka S, Tsukita K, Naitoh M, Takahashi K, Yamamoto T, Adachi F, Kondo T, Okita K, Asaka I, Aoi T, Watanabe A, Yamada Y, Morizane A, Takahashi J, Ayaki T, Ito H, Yoshikawa K, Yamawaki S, Suzuki S, Watanabe D, Hioki H, Kaneko T, Makioka K, Okamoto K, Takuma H, Tamaoka A, Hasegawa K, Nonaka T, Hasegawa M, Kawata A, Yoshida M, Nakahata T, Takahashi R, Marchetto M C, Gage F H, Yamanaka S, Inoue H (2012) Drug screening for ALS using patient-specific induced pluripotent stem cells. *Science translational medicine* 4: 145ra104

Grimm S (2004) The art and design of genetic screens: mammalian culture cells. *Nat Rev Genet* 5: 179-189

Hauswirth W W, Aleman T S, Kaushal S, Cideciyan A V, Schwartz S B, Wang L, Conlon T J, Boye S L, Flotte T R, Byrne B J, Jacobson S G (2008) Treatment of leber congenital amaurosis due to RPE65 mutations by ocular subretinal injection of adeno-associated virus gene vector: short-term results of a phase I trial. *Hum Gene Ther* 19: 979-990

Jacobson S G, Cideciyan A V, Ratnakaram R, Heon E, Schwartz S B, Roman A J, Peden M C, Aleman T S, Boye S L, Sumaroka A, Conlon T J, Calcedo R, Pang J J, Erger K E, Olivares M B, Mullins C L, Swider M, Kaushal S, Feuer W J, Iannaccone A, Fishman G A, Stone E M, Byrne B J, Hauswirth W W (2012) Gene therapy for leber congenital amaurosis caused by RPE65 mutations: safety and efficacy in 15 children and adults followed up to 3 years. *Arch Ophthalmol* 130: 9-24

Krock B L, Bilotta J, Perkins B D (2007) Noncell-autonomous photoreceptor degeneration in a zebrafish model of choroideremia. *Proc Natl Acad Sci USA* 104: 4600-4605

Liao J L, Yu J, Huang K, Hu J, Diemer T, Ma Z, Dvash T, Yang X J, Travis G H, Williams D S, Bok D, Fan G (2010) Molecular signature of primary retinal pigment epithelium and stem-cell-derived RPE cells. *Human molecular genetics* 19: 4229-4238

Maguire A M, High K A, Auricchio A, Wright J F, Pierce E A, Testa F, Mingozzi F, Bennicelli J L, Ying G S, Rossi S, Fulton A, Marshall K A, Banfi S, Chung D C, Morgan J I, Hauck B, Zelenaia O, Zhu X, Raffini L, Coppieters F, De Baere E, Shindler K S, Volpe N J, Surace E M, Acerra C, Lyubarsky A, Redmond T M, Stone E, Sun J, McDonnell J W, Leroy B P, Simonelli F, Bennett J (2009) Age-dependent effects of RPE65 gene therapy for Leber's congenital amaurosis: a phase 1 dose-escalation trial. *Lancet* 374: 1597-1605

Maguire A M, Simonelli F, Pierce E A, Pugh E N, Jr., Mingozzi F, Bennicelli J, Banfi S, Marshall K A, Testa F, Surace E M, Rossi S, Lyubarsky A, Arruda V R, Konkle B, Stone J, Sun J, Jacobs J, Dell'Osso L, Hertle R, Ma J X, Redmond T M, Zhu X, Hauck B, Zelenaia O, Shindler K S, Maguire M G, Wright J F, Volpe N J, McDonnell J W, Auricchio A, High K A, Bennett J (2008) Safety and efficacy of gene transfer for Leber's congenital amaurosis. *N Engl J Med* 358: 2240-2248

Marlhens F, Bareil C, Griffoin J-M, Zrenner E, Amalric P, Eliaou C, Liu S-Y, Harris E, Redmond T M, Arnaurd B, Claustres M, Hamel C P (1997) Mutations in RPE65 cause Leber's congenital amaurosis. *Nat Genet* 17: 139-141

Mussolino C, della Corte M, Rossi S, Viola F, Di Vicino U, Marrocco E, Neglia S, Doria M, Testa F, Giovannoni R, Crasta M, Giunti M, Villani E, Lavitrano M, Bacci M L, Ratiglia R, Simonelli F, Auricchio A, Surace E M (2011) AAV-mediated photoreceptor transduction of the pig cone-enriched retina. *Gene Ther* 18: 637-645

Nguyen UTT, Wu Y, Goodall A, Alexandrov K (2010) Analysis of Protein Prenylation In Vitro and In vivo Using Functionalized Phosphoisoprenoids. *Current Protocols in Protein Science* 62: 14.13.11-14.13.15

Park I H, Zhao R, West J A, Yabuuchi A, Huo H, Ince T A, Lerou P H, Lensch M W, Daley G Q (2008) Reprogramming of human somatic cells to pluripotency with defined factors. *Nature* 451: 141-146

Ramirez J M, Bai Q, Pequignot M, Becker F, Kassambara A, Bouin A, Kalatzis V, Dijon-Grinand M, De Vos J (2013) Side scatter intensity is highly heterogeneous in undifferentiated pluripotent stem cells and predicts clonogenic self-renewal. *Stem Cells Dev* 22: 1851-1860

Seabra M C, Brown M S, Slaughter C A, Sudhof T C, Goldstein J L (1992) Purification of component A of Rab geranylgeranyl transferase: possible identity with the choroideremia gene product. *Cell* 70: 1049-1057

Seabra M C, Ho Y K, Anant J S (1995) Deficient geranylgeranylation of Ram/Rab27 in choroideremia. *J Biol Chem* 270: 24420-24427

Siegel S, Castellan N J (1988) *Non parametric statistics for the behavioral sciences*, New York: McGraw-Hill.

Singh R, Shen W, Kuai D, Martin J M, Guo X, Smith M A, Perez E T, Phillips M J, Simonett J M, Wallace K A, Verhoeven A D, Capowski E E, Zhang X, Yin Y, Halbach P J, Fishman G A, Wright L S, Pattnaik B R, Gamm D M (2013) iPS cell modeling of Best disease: insights into the pathophysiology of an inherited macular degeneration. *Hum Mol Genet* 22: 593-607

Sparrow J R, Hicks D, Hamel C P (2010) The retinal pigment epithelium in health and disease. *Curr Mol Med* 10: 802-823

Takahashi K, Tanabe K, Ohnuki M, Narita M, Ichisaka T, Tomoda K, Yamanaka S (2007) Induction of pluripotent stem cells from adult human fibroblasts by defined factors. *Cell* 131: 861-872

Tolmachova T, Tolmachov O E, Barnard A R, de Silva S R, Lipinski D M, Walker N J, Maclaren R E, Seabra M C (2013) Functional expression of Rab escort protein 1 following AAV2-mediated gene delivery in the retina of choroideremia mice and human cells ex vivo. *J Mol Med (Berl)* 91: 825-837

Tolmachova T, Tolmachov O E, Wavre-Shapton S T, Tracey-White D, Futter C E, Seabra M C (2012) CHM/REP1 cDNA delivery by lentiviral vectors provides functional expression of the transgene in the retinal pigment epithelium of choroideremia mice. *J Gene Med* 14: 158-168

Tolmachova T, Wavre-Shapton S T, Barnard A R, MacLaren R E, Futter C E, Seabra M C (2010) Retinal pigment epithelium defects accelerate photoreceptor degeneration in cell type-specific knockout mouse models of choroideremia. *Invest Ophthalmol Vis Sci* 51: 4913-4920

Tucker B A, Park I H, Qi S D, Klassen H J, Jiang C, Yao J, Redenti S, Daley G Q, Young M J (2011) Transplantation of adult mouse iPS cell-derived photoreceptor precursors restores retinal structure and function in degenerative mice. *PLoS One* 6: e18992

Vandenberghe L H, Auricchio A (2012) Novel adeno-associated viral vectors for retinal gene therapy. *Gene Ther* 19: 162-168

Vandenberghe L H, Bell P, Maguire A M, Cearley C N, Xiao R, Calcedo R, Wang L, Castle M J, Maguire A C, Grant R, Wolfe J H, Wilson J M, Bennett J (2011) Dosage thresholds for AAV2 and AAV8 photoreceptor gene therapy in monkey. *Science translational medicine* 3: 88ra54

Vasireddy V, Mills J A, Gaddameedi R, Basner-Tschakarjan E, Kohnke M, Black A D, Alexandrov K, Zhou S, Maguire A M, Chung D C, Mac H, Sullivan L, Gadue P, Bennicelli J L, French D L, Bennett J (2013) AAV-Mediated Gene Therapy for Choroideremia: Preclinical Studies in Personalized Models. *PLoS One* 8: e61396

Weber M, Rabinowitz J, Provost N, Conrath H, Folliot S, Briot D, Cherel Y, Chenuaud P, Samulski J, Moullier P, Rolling F (2003) Recombinant adeno-associated virus serotype 4 mediates unique and exclusive long-term transduction of retinal pigmented epithelium in rat, dog, and nonhuman primate after subretinal delivery. *Mol Ther* 7: 774-781

Wu Y W, Alexandrov K, Brunsveld L (2007) Synthesis of a fluorescent analogue of geranylgeranyl pyrophosphate and its use in a high-throughput fluorometric assay for Rab geranylgeranyltransferase. *Nature protocols* 2: 2704-2711

Yu J, Thomson J A (2008) Pluripotent stem cell lines. *Genes Dev* 22: 1987-1997

Yu J, Vodyanik M A, Smuga-Otto K, Antosiewicz-Bourget J, Frane J L, Tian S, Nie J, Jonsdottir G A, Ruotti V, Stewart R, Slukvin, II, Thomson J A (2007) Induced pluripotent stem cell lines derived from human somatic cells. *Science* 318: 1917-1920

The invention claimed is:

1. A method for selectively expressing a polynucleotide of interest in the retinal pigment epithelium in an eye of a human subject in need thereof by transducing the retinal pigment epithelium with an amount of a rAAV2/5 vector containing the polynucleotide of interest.

2. The method of claim 1 wherein the rAAV2/5 vector comprises a CAG promoter.

3. The method of claim 1 wherein the subject is affected or likely to be affected with a retinal disease affecting the retinal pigment epithelium selected from the group consisting of inherited or non-inherited retinal degenerations, retinal dystrophies, retinitis pigmentosa, macular degenerations, Leber's congenital amaurosis (LCA), cone-rod dystrophies, neovascular diseases of the eye, choroidal degenerations, choroidal sclerosis, diabetic retinopathies, proliferative vitreoretinopathies, choroideremia, glaucoma and metabolic disorders such as Sly syndrome (MPS VII) and gyrate atrophy, retinal detachment or injury.

4. The method of claim 1 wherein the polynucleotide of interest is used for gene replacement therapy and is selected from the group consisting of RGR, RDH5, RPE65, RLBP1, MERTK, LRAT, REP1, RBP4, ELOVL4, EFEMPI, BEST1, TIMP3, AIPL1, and CRB1.

5. The method of claim 1 wherein the polynucleotide of interest encodes RLBP1.

6. The method of claim 1 wherein the polynucleotide of interest encodes REP1.

7. The method of claim 1 wherein the polynucleotide of interest encodes a neurotrophic factor.

8. The method of claim 1 wherein the polynucleotide of interest encodes a neurotrophic factor selected in the group consisting of bFGF, aFGF, BDNF, CNTF, IL-1beta, NT-3, IGF-II, GDNF, NGF and RdCVF.

9. The method of claim 1 wherein the polynucleotide product of interest is a site-specific endonuclease that provides for site-specific knock-down of gene function.

10. The method of claim 1 wherein the polynucleotide product of interest is a site-specific endonuclease that provides for site-specific knock-down of gene function selected in the group consisting of zinc finger nucleases (ZFNs) and transcription activator-like effector nucleases (TALENS).

11. The method of claim 1 wherein the polynucleotide product of interest is an interfering RNA (RNAi).

12. A rAAV2/5 vector containing a polynucleotide of interest selected in the group of RGR, RDH5, RPE65, RLBP1, MERTK, LRAT, REP1, RBP4, ELOVL4, EFEMPI, BEST1, TIMP3, AIPL1, and CRB1, wherein the polynucleotide is under the control of a CAG promoter.

13. The rAAV2/5 vector of claim 12 wherein the polynucleotide encodes RLBP1.

14. The rAAV2/5 vector of claim 12 wherein the polynucleotide encodes REP1.

15. A method for treating retinitis pigmentosa in a human subject in need thereof comprising administering to the human subject a therapeutically effective amount of a rAAV2/5 vector containing a polynucleotide encoding RLBP1 to transduce the retinal pigment epithelium.

16. A method for treating choroideremia in a human subject in need thereof comprising administering to the human subject a therapeutically effective amount of a rAAV2/5 vector containing a polynucleotide encoding REP1 to transduce the retinal pigment epithelium.

* * * * *